United States Patent
Fan et al.

(10) Patent No.: US 10,532,982 B2
(45) Date of Patent: Jan. 14, 2020

(54) PROCESSES AND INTERMEDIATES IN THE PREPARATION OF C5AR ANTAGONISTS

(71) Applicant: CHEMOCENTRYX, INC., Mountain View, CA (US)

(72) Inventors: Pingchen Fan, Fremont, CA (US); Jaroslaw Kalisiak, Mountain View, CA (US); Antoni Krasinski, Sunnyvale, CA (US); Rebecca M. Lui, Santa Clara, CA (US); Jay Powers, Pacifica, CA (US); Sreenivas Punna, Sunnyvale, CA (US); Hiroko Tanaka, Mountain View, CA (US); Penglie Zhang, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 16/360,195

(22) Filed: Mar. 21, 2019

(65) Prior Publication Data

US 2019/0276402 A1    Sep. 12, 2019

Related U.S. Application Data

(60) Continuation of application No. 15/659,468, filed on Jul. 25, 2017, now Pat. No. 10,266,492, which is a division of application No. 14/867,669, filed on Sep. 28, 2015, now Pat. No. 9,745,268.

(60) Provisional application No. 62/057,107, filed on Sep. 29, 2014.

(51) Int. Cl.
C07D 211/60 (2006.01)

(52) U.S. Cl.
CPC ................... C07D 211/60 (2013.01)

(58) Field of Classification Search
USPC .......................................................... 546/26
See application file for complete search history.

(56) References Cited

U.S. PATENT DOCUMENTS

| | | | |
|---|---|---|---|
| 4,686,100 A | 8/1987 | Raffin et al. | |
| 6,713,502 B2 | 3/2004 | Dhanak et al. | |
| 7,105,567 B2 | 9/2006 | Ishibuchi et al. | |
| 7,169,775 B2 | 1/2007 | Thurkauf et al. | |
| 7,455,837 B2 | 11/2008 | Guo et al. | |
| 7,635,698 B2 | 12/2009 | Rosse et al. | |
| 7,834,035 B2 | 11/2010 | Bessis et al. | |
| 8,007,767 B2 | 8/2011 | Thurkauf et al. | |
| 8,026,367 B2 | 9/2011 | Allegretti et al. | |
| 8,198,454 B2 | 6/2012 | Nakamura et al. | |
| 8,206,716 B2 | 6/2012 | Fung et al. | |
| 8,372,404 B2 | 2/2013 | Fung et al. | |
| 8,445,515 B2 | 5/2013 | Fan et al. | |
| 8,906,938 B2 | 12/2014 | Fan et al. | |
| 9,126,939 B2 | 9/2015 | Fan et al. | |
| 9,573,897 B2 | 2/2017 | Fan et al. | |
| 9,745,268 B2* | 8/2017 | Fan ...................... | C07D 211/60 |
| 10,035,768 B2 | 7/2018 | Fan et al. | |
| 10,266,492 B2* | 4/2019 | Fan ...................... | C07D 211/60 |
| 2003/0195192 A1 | 10/2003 | Haviv et al. | |
| 2003/0195195 A1 | 10/2003 | Haviv et al. | |
| 2004/0014744 A1 | 1/2004 | Haviv et al. | |
| 2004/0014782 A1 | 1/2004 | Krause | |
| 2006/0004049 A1 | 1/2006 | Yao et al. | |
| 2006/0019995 A1 | 1/2006 | Rault et al. | |
| 2006/0030557 A1 | 2/2006 | Haviv et al. | |
| 2006/0154917 A1 | 7/2006 | Zhang et al. | |
| 2007/0117802 A1 | 5/2007 | Borzilleri et al. | |
| 2010/0074863 A1 | 3/2010 | Or et al. | |
| 2010/0104558 A1 | 4/2010 | Tharaux et al. | |
| 2010/0179150 A1 | 7/2010 | Basarab et al. | |
| 2010/0190824 A1 | 7/2010 | Kumar et al. | |
| 2010/0311753 A1 | 12/2010 | Fan et al. | |
| 2011/0275639 A1 | 11/2011 | Fan et al. | |
| 2012/0225056 A1 | 9/2012 | Rother et al. | |
| 2013/0317028 A1 | 11/2013 | Fan et al. | |
| 2015/0126492 A1 | 5/2015 | Dechantsreiter et al. | |
| 2015/0141425 A1 | 5/2015 | Fan et al. | |
| 2017/0065604 A1 | 3/2017 | Fan et al. | |
| 2017/0114017 A1 | 4/2017 | Fan et al. | |
| 2017/0202821 A1 | 7/2017 | Bekker | |
| 2019/0060321 A1 | 2/2019 | Fan et al. | |
| 2019/0062275 A1 | 2/2019 | Fan et al. | |

FOREIGN PATENT DOCUMENTS

| | | |
|---|---|---|
| WO | 00/12074 A2 | 3/2000 |
| WO | 00/12074 A3 | 3/2000 |
| WO | 02/049993 A2 | 6/2002 |
| WO | 02/049993 A3 | 6/2002 |
| WO | 03/029187 A1 | 4/2003 |
| WO | 03/082826 A1 | 10/2003 |
| WO | 03/082828 A1 | 10/2003 |
| WO | 03/084524 A1 | 10/2003 |
| WO | 2004/018460 A1 | 3/2004 |

(Continued)

OTHER PUBLICATIONS

U.S. Appl. No. 10/266,492, dated Apr. 23, 2019, Fan et al., parent.
Extended European Search Report corresponding to EP 09835688.4 (PCT/US2009/068941) dated Aug. 2, 2012, 5 pages.
Extended European Search Report corresponding to EP 11799027.5 (PCT/US2011/041910) dated Dec. 18, 2013, 4 pages.
Extended European Search Report corresponding to EP 16167779.4 dated Jun. 30, 2016; 6 pages.
Extended European Search Report corresponding to EP 15845610.3 dated May 16, 2018; 18 pages.

(Continued)

*Primary Examiner* — Nizal S Chandrakumar

(74) *Attorney, Agent, or Firm* — Mintz Levin Cohn Ferris Glovsky and Popeo PC

(57) ABSTRACT

Intermediates and methods are provided for the preparation of selected C5aR antagonist compounds.

1 Claim, 4 Drawing Sheets

(56) References Cited

FOREIGN PATENT DOCUMENTS

| WO | 2004/043925 A2 | 5/2004 |
|---|---|---|
| WO | 2004/043925 A3 | 5/2004 |
| WO | 2004/100975 A1 | 11/2004 |
| WO | 2004/110996 A1 | 12/2004 |
| WO | 2005/007087 A2 | 1/2005 |
| WO | 2005/007087 A3 | 1/2005 |
| WO | 2006/012226 A2 | 2/2006 |
| WO | 2006/012226 A3 | 2/2006 |
| WO | 2007/051062 A2 | 5/2007 |
| WO | 2008/022060 A2 | 2/2008 |
| WO | 2008/022060 A3 | 2/2008 |
| WO | 2010/019210 A2 | 2/2010 |
| WO | 2010/019210 A3 | 2/2010 |
| WO | 2010/025510 A1 | 3/2010 |
| WO | 2010/075257 A1 | 7/2010 |
| WO | 2011/035143 A2 | 3/2011 |
| WO | 2011/163640 A1 | 12/2011 |

OTHER PUBLICATIONS

Extended European Search Report corresponding to EP 19154555.7 dated Apr. 17, 2019; 6 pages.

International Search Report corresponding to PCT/US2009/068941 dated Mar. 5, 2010; 1 page.

International Preliminary Report on Patentability corresponding to PCT/US2009/068941 dated Jun. 29, 2011, 8 pages.

International Search Report corresponding to PCT/US2011/041910 dated Nov. 15, 2011, 1 page.

International Preliminary Report on Patentability corresponding to PCT/US2011/041910 dated Dec. 28, 2012, 8 pages.

International Search Report and Written Opinion corresponding to PCT Application No. PCT/US2015/052697 dated Jan. 7, 2016, 8 pages.

International Preliminary Report on Patentability corresponding to PCT/US2015/052697 dated Apr. 13, 2017, 6 pages.

International Search Report and Written Opinion corresponding to PCT/US2017/013132 dated Apr. 7, 2017; 10 pages.

Abdellatif, A. A. et al, "True vasculitis in lupus nephritis," *Clinical Nephrology* (Aug. 2010; accepted in revised form Jan. 22, 2010); 74(2):106-112.

Aboab et al., "Emerging drugs for the treatment of sepsis," *Exp. Opin. Emerg. Drugs.* (10.1517/14728214.11.1.7 © 2006 Ashley Publications SSN 1472-8214); 11(1):7-22.

Alexander, Jessy John et al., "Contrasting roles for CR3 and C5aR in experimental immune complex-mediated glomerulonephritis," *Molecular Immunology* Abstract Only (Oct. 2014); 61(2):246 Abstract No. 083.

Allegretti, Marcello et al., "Allosteric Modulation of Chemoattractant Receptors," *Frontiers in Immunology* (May 2, 2016); vol. 7, Article 170; 9 pages.

Ayala et al., "Differential induction of apoptosis in lymphoid tissues during sepsis: variation in onset, frequency and the nature of the mediators," *Blood* (May 15, 1996); 87:4261-4275.

Bao et al., "C5a promotes development of experimental lupus nephritis which can be blocked with a specific receptor antagonist," *Eur. J. Immunol.* (Accepted Jun. 20, 2005); 35:2496-2506.

Bekker, Pirow et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study," *PLOS One* [DOI:10.1371/journal.pone.0164646 (Oct. 21, 2016); 19 pages.

Blagg et al., "Small, non-peptide C5a receptor antagonists: Part 1," *Bioorganic & Medicinal Chemistry Letters* (Aug. 31, 2008); 18:5601-5604.

Braga et al., "Making crystals from crystals: a green route to crystal engineering and polymorphism," *The Journal of The Royal Society of Chemistry, Chem. Commun.* (Jun. 15, 2005), pp. 3635-3645.

Brodbeck; Robbin M. et al., "Identification and Characterization of NDT 9513727 [*N,N*-bis(1,3-Benzodioxol-5-ylmethyl)-1-butyl-2,4-diphenyl-*1H*-imidazole-5-methanamine], a Novel, Orally Bioavailable C5a Receptor Inverse Agonist," *The Journal of Pharmacology and Experimental Therapeutics* (2008; accepted Aug. 26, 2008); 327(3):898-909.

CAS Registry 1346623-17-3, also known as CCX168, copy of STN entry for registry number, accessed Mar. 31, 2018, 1 page (Year: 2018).

Chemcats (AN) 0078873838 (Jul. 29, 2011); one page.

ChemiCool "rotamer," (Sep. 9, 2012) one page.

Chronic-Obstructive-Pulmonary disease (COPD), Treatment Overview, www.webmd.com/lung/copd/tc/chronic-obstructive-pulmonary-disease-copd-treatme . . . p. 1-2, retrieved Apr. 22, 2014.

Cravedi et al., "Immune Cell-Derived C3a and C5a Costimulate Human T Cell Alloimmunity" *Am. J. Transplant* (Jun. 27, 2013); 13(10):2530-2539.

Dairaghi D.J. et al., "Chemokine Receptor CCR3 Function Is Highly Dependent on Local pH and Ionic Strength," *The Journal of Biological Chemistry* (Nov. 7, 1997); 272(45):28206-28209.

Dairaghi D.J. et al., "HHV8-encoded vMIP-I selectively Engages Chemokine Receptor CCR8 Agonist and Antagonist Profiles of Viral Chemokines," *The Journal of Biological Chemistry*, (Jul. 30, 1999); 274(31):21569-21574.

Drugnews, "CCX168 ChemoCentryx Identifies C5a receptor antagonist GlaxoSmithKline milestone payment ChemoCentryx milestone payment," R & D Focus Drug News, May 2009, pp. 1-2, http://business. hgihbeam.com/436989/article-1G1-199837927/ccx-168-chemocentryx-identi . . ., retrieved Sep. 5, 2015.

Gerber B. O. et al., "An Activation Switch in the Ligand Binding Pocket of the C5a Receptor," *The Journal of Biological Chemistry* (Feb. 2, 2001); 276(5):3394-3400.

Guan, Li Ping et al., "Synthesis and Anticonvulsant Activity of 5-Phenyl-[1,2,4]-triazolo[4,3-a)quinolones," *Arch. Pharm. Chem. Life Sci.* (2008; accepted Jul. 30, 2008); 341:774-779.

Horiuchi, Takahiko et al., "Complement-targeted therapy: development of C5- and C5a-targed inhibition," *Inflammation and Regeneration* (published online Jun. 3, 2016); 36(11): 1-6.

Hu et al., "Small molecules in treatment of sepsis," *Current Drug Targets*, (Feb. 2011; DOI:10.2174/138945011794182737); 12:256-262.

Huber-Lang et al., "Protection of innate immunity by C5aR antagonist in septic mice," *The FASEB Journal* (Oct. 2002; accepted Jun. 26, 2002) 16:1567-1574.

Huber-Lang et al., "Role of Complement in Multi-Organ Dysfunction Syndrome," *The Complement System*, Abstract, (© 2004; Print/DOI: 10.1007/1-4020-8056-5_22); pp. 465-480.

"Improper Markush," (Feb. 9, 2011); Fed. Registry 76(27):7162-7175, slide 1, 64-67.

Inflammation, Wikipedia, https://en.wikipedia.org/wiki/inflammation (retrieved Sep. 7, 2015); 30 pages.

"Ischemia-reperfusion injury in vascular disease," Sebastian de la Fuente, Apr. 2009, 54 pages.

Jayne et al., "Oral C5A Receptor Antagonist CCX168 Phase 2 Clinical Trial in ANCA-Associated Renal Vasculitis", *Ann Rheum Dis* (2014; DOI 10.1136/annrheumdis-2014-eular.3728): 73(2):148.

Kumar et al., "Cell-derived anaphylatoxins as key mediators of antibody-dependent type II autoimmunity in mice," *J. Clin. Invest.*, (Feb. 2006; accepted in revised form Nov. 15, 2005); 116(2):512-520.

Kusner et al., "Effect of complement and its regulation on myasthenia gravis pathogenesis," *Expert Rev. Clin. Immunol.* (Jan. 2008; doi:10.1586/1744666X.4.1.43); 4(1):43-52.

Lachmann, P. J. et al., "Taking Complement to the Clinic—has the Time Finally Come?," *Scandinavian Journal of Immunology* (pub online Apr. 1, 2009); 69:471-478.

Lally, Lindsay et al., "Current Therapies for ANCA-Associated Vasculitis," *Annu. Rev. Med.* (2015; first published online Oct. 17, 2014); 66:227-240.

Lee, Hyun et al., "Receptors for complement C5a. The importance of C5aR and the enigmatic role of C5L2," *Immunol. Cell Biol.* (published online Jan. 29, 2008); 86(2):153-160.

Le Quintrec, Moglie, M.D., Ph.D., "Ecullizumab for Treatment of Rapidly Progressive C3 Glomerulopathy," *Am J Kidney Dis.* (2015; originally published on-line Dec. 16, 2014); 65(3):484-489.

(56) References Cited

OTHER PUBLICATIONS

Lupus Nephritis Definition *Wikipedia* https://en.wikipedia.org/wiki/Lupus_nephritis (May 26, 2017); 3 pages.
March, Darren R. et al., "Potent Cyclic Antagonists of the Complement C5a Receptor on Human Polymorphonuclear Leukocytes. Relationships between Structures and Activity," *Molecular Pharmacology* (2004; accepted Jan. 7, 2004); 65(4):868-879.
MedlinePlus "Sepsis," (Apr. 5, 2012); 3 pages.
Mizuno et al., "Novel C5a regulators in inflammatory disease," *Exp. Opin. Investig. Drugs* (Jul. 15, 2005);14(7):807-821.
Monk, P.N. et al., "Function, structure and therapeutic potential of complement C5a receptors," *British Journal of Pharmacology* (Jul. 2, 2007); 152:429-448.
Nikforovich et al., "Modeling Molecular Mechanisms of Binding of the Anaphylatoxin C5 to the C5a Receptor," *Biochemistry* (Jan. 11, 2008); 47:3117-3130.
Noël, Romain, et al., "Synthesis of New Chiral 6-Carbonyl 2,3,8,8a-Tetrahydro-7H-oxazolo[3,2-α]pyridines," *J. Org. Chem.* (Oct. 1, 2005); 70(22):9044-9047.
Noël, Romain, et al., "Diastereoselective Reduction of Bicyclic β-Enamino Carbonyl Piperidines—Application to the Total Syntehsis of (-)-Deoocassine," *Eur. J. Org. Chem.* (2007; published online Nov. 17, 2006 DOI: 10.1002/ejoc.200600777); 476-486.
Noël, Romain, et al., "Convenient One-Pot Synthesis of Chiral Tetrahydropyridines via a Multicomponent Reaction," *Synthesis* (2008; advanced online publication May 16, 2008); 12:1948-1954.
Osoda, Tsutomu et al., "2D-Qsar for 450 types of amino acid induction peptides with a novel substructure pair descriptor having wider scope," *Journal of Cheminformatics* (Nov. 2, 2011);3:50; 9 pages.
Paczkowski et al., "Pharmacological characterization of antagonists of the C5a receptor," *British J. of Pharmacology* (Sep. 13, 1999); 128:1461-1466.
Powers, Larry J. et al., "Effect of Structural Change on Acute Toxicity and Antiinflammatory Activity in a Series of Imidazothiazoles and Thiazolobenzimidazoles," *Journal of Medicine Chemistry* (Jan. 1, 1981) 24(5):604-609.
Penfold M.E.T. et al., "Cytomegalovirus encodes a potent a chemokine," *Proc. Natl. Acad. Sci. USA* (Aug. 1999; rec'd for review Apr. 20, 1999); 96:9839-9844.
Press Release: ChemoCentryx Announces Presentation of Positive Results from Phase II ANCA-Associated Vasculitis Clear Trial of Orally Administered Complement 5a Receptor Inhibitor CCX168 at the 53$^{rd}$ ERA-EDTA Congress (May 23, 2016); 5 pages.
Press Release: ChemoCentryx Announces Presentation of Positive Data from Ongoing Pilot Phase II Trial of CCX168 (Avacopan) in Atypical Hemolytic Uremic Syndrome (AHUS) at ASN Kidney Week 2016 (Oct. 17, 2016); 3 pages.
Proctor, Lavinia M. et al., "Recent development in C5/C5a inhibitors," *Expert Opinion on Therapeutic Patents* (Mar. 24, 2006); 16(4):445-458.
PubChem-CID-58506549; Create date Aug. 19, 2012, p. 3 Fig.
PubChem-CID-58506538; Create date Aug. 19, 2012, p. 3, Fig.
PubChem-CID-68717675; Create date Nov. 30, 2012, p. 3, Fig.
PubChem-CID-68607180; Create date Nov. 30, 2012, p. 3, Fig.
Qu et al., "Recent developments in low molecular weight complement inhibitors," *Molecular Immun.* (Aug. 28, 2009); 47:185-195.
Rheumatoid Arthritis Definition *Johns Hopkins Arthritis Center* https://www.hopkinsarthritis.org/arthritis-info/rheumatoid-arthritis/ra-treatment/ (May 26, 2017); 3 pages.
Ricklin, Daniel et al., "Complement-targeted therapeutics," *Nature Biotechnology* (pub online Nov. 7, 2007); 25(11):1265-1275.
Ricklin, Daniel et al., "Complement in immune and inflammatory disorders: therapeutic interventions," *J. Immunol.* (Apr. 15, 2013); 190(8):3839-3847).
Riedemann et al., "The enigma of sepsis," *The Journal of Clinical Investigation* (Aug. 15, 2003); 112(4):460-467.
Rittirsch et al., "Harmful molecular mechanisms in sepsis," *Nat. Rev. Immunol.* (Oct. 2008; DOI: 10.1038/nri2402); 8(10):776-787.
RN 1348614-10-7 Database:GVK BIO (2011).

Sarma et al., "New developments in C5a receptor signaling," *Cell Health Cytoskelet.* (Jul. 31, 2012); 4:73-82.
Seddon, "Pseudopolymorph: A Polemic," *Crystal Growth & Design* (Jul. 26, 2004); 4(6):1087.
Short et al., "Effects of a new C5a receptor antagonist on C5a- and endotoxin-induced neutropenia in the rat," *British J. Pharma.* (1999; accepted Nov. 5, 1998); 125:551-554.
Short, Anna J. et al., "Response-selective C5a agonists: differential effects on neutropenia and hypotension in the rat," *British J. Pharma* (1999; accepted Jul. 21, 1999); 128:511-514.
Siciliano, Salvatore J. et al., "Two-site binding of C5a by its receptor: An alternative binding paradigm for G protein-coupled receptors," *Proc. Natl. Acad. Sci. USA* (Feb. 1994; communicated by E. Scolnick Oct. 20, 1993); 91:1214-1218.
Sridharan, Vellaisamy et al., "A Very Efficient Cerium(IV) Ammonium Nitrate Catalyzed, Four-Component Synthesis of Tetrahydropyridines and Its Application in the Concise Generation of Functionalized Homoquinolizine Frameworks," *Chem Eur. J.* (published online Mar. 13, 2009; DOI:10.1002/CHEM.200900044); 15;4565-4572.
Strachan Anna J. et al., "A New Small Molecule C5a Receptor Antagonist Inhibits the Reverse-Passive Arthus Reaction and Endotoxic Shock in Rats," The Journal of Immunology, (Apr. 6, 2000); 164:6560-6565.
Sumichika Hiroshi. et al., "Identification of a Potent and Orally Active Non-peptide C5a Receptor Antagonist," *The Journal of Biological Chemistry*, Dec. 20, 2002, vol. 277, No. 51, pp. 49403-49407.
Taylor, Stephen M. et al., "Development of response-selective agonists of human C5a anaphylatoxin: conformational, biological, and therapeutic considerations," Current Med. Chem., (© 2001 Bentham Science Publishers Ltd); 8:675-684.
"Chapter 6: Treatment of Acute Rejection," *American Journal of Transplantation* (Sep. 24, 2009); 9(3):S21-S22.
Unsinger, Jacqueline et al., "Sepsis-induced human lymphocyte apoptosis and cytokine production in "humanized" mice," *Journal of Leukocyte Biology* (Aug. 2009; accepted Mar. 16, 2009); 86: 219-227.
Ward, "Role of the complement in experimental sepsis," *Journal of Leukocyte Biology*, (Mar. 2008; published online Sep. 17, 2007); 83:467-470.
Ward, "The Harmful Role of C5a on Innate Immunity in Sepsis," *J. Innate Immun.* (Jun. 26, 2010); 2:439-445.
Ward et al., "The dark side of C5a in sepsis," *Nature Reviews* (Feb. 2004); 4:133-142.
Warren, "Mouse models to study sepsis syndrome in humans" *J. Leukocyte Biol.* (Apr. 15, 2009); 86:199-200.
Woltering, Thomas J. et al., "Synthesis and characterization of 1,3-dihydro-benzo[b][1,4]diazepin-2-one derivatives: Part 4. In vivo active potent and selective non-competitive metabotropic glutamate receptor 2/3 antagonists," *Bioorganic & Medicine Chemistry Letters* (Dec. 1, 2010) 20:6969-6974.
Woodruff et al., "Species dependence for binding of small molecule agonist and antagonists to the C5a receptor on polymorphonuclear leukocytes," *Inflammation* (2001; DOI:10.1023/A:1011036414353); 25(3):171-177.
Woodruff T.M. et al., "A Potent Human C5a Receptor Antagonist Protects against Disease Pathology in a Rat Model of Inflammatory Bowel Disease," *The Journal of Immunology* (Nov. 15, 2003); 171:5514-5520.
Wygnaarden et al., Textbook of medicine, 16th Edition, © 1983, p. 247.
Xiao et al., "C5a Receptor (CD88) Blockade Protects against MPO-ANCA GN," *J. Am. Soc. Nephrol.* (2014; accepted for publication Aug. 5, 2013); 25(2):225-231.
Yan et al., "New insights for C5a and C5a receptors in sepsis," *Frontiers in Immunology* (Dec. 10, 2012); 3(368):1-15.
Yatime, Laure et al., "Structural basis for the targeting of complement anaphylatoxin C5a using a mixed $_L$-RNA/$_L$-DNA aptamer," *Nature Communications* (Apr. 22, 2015); 13 pages.

* cited by examiner

Scheme 1:

Scheme 2:

Scheme 3:

PROCESSES AND INTERMEDIATES IN THE PREPARATION OF C5AR ANTAGONISTS

CROSS-REFERENCES TO RELATED APPLICATIONS

This application is a continuation of U.S. patent application Ser. No. 15/659,468 filed Jul. 25, 2017, which is a divisional of U.S. patent application Ser. No. 14/867,669 filed Sep. 28, 2015 (now U.S. Pat. No. 9,745,268), which application claims the benefit of priority to U.S. Provisional Application Ser. No. 62/057,107, filed Sep. 29, 2014, each of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The complement system plays a central role in the clearance of immune complexes and in immune responses to infectious agents, foreign antigens, virus infected cells and tumor cells.

Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., *J. Immunol.* 99: 1211-1216 (1967)). It is composed of two polypeptide chains, α and β, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulphide bond as well as noncovalent interactions (Ooi, Y. M. et al., *J. Immunol.* 124: 2494-2498 (1980)).

C5 is cleaved into the C5a and C5b fragments during activation of the complement pathways. The convertase enzymes responsible for C5 activation are multi-subunit complexes of C4b, C2a, and C3b for the classical pathway and of $(C3b)_2$, Bb, and P for the alternative pathway (Goldlust, M. B. et al., *J. Immunol.* 113: 998-1007 (1974); Schreiber, R. D. et al, *Proc. Natl. Acad. Sci.* 75: 3948-3952 (1978)). C5 is activated by cleavage at position 74-75 (Arg-Leu) in the α-chain. After activation, the 11.2 kD, 74 amino acid peptide C5a from the amino-terminus portion of the α-chain is released. Both C5a and C3a are potent stimulators of neutrophils and monocytes (Schindler, R. et al., *Blood* 76: 1631-1638 (1990); Haeffner-Cavaillon, N. et al., *J. Immunol.* 138: 794-700 (1987); Cavaillon, J. M. et al., *Eur. J. Immunol.* 20: 253-257 (1990)).

In addition to its anaphylatoxic properties, C5a induces chemotactic migration of neutrophils (Ward, P. A. et al., *J. Immunol.* 102: 93-99 (1969)), eosinophils (Kay, A. B. et al., *Immunol.* 24: 969-976 (1973)), basophils (Lett-Brown, M. A. et al., *J. Immunol.* 117: 246-252 1976)), and monocytes (Snyderman, R. et al., *Proc. Soc. Exp. Biol. Med.* 138: 387-390 1971)).

The anaphylactic and chemotactic effects of C5a are believed to be mediated through its interaction with the C5a receptor. The human C5a receptor (C5aR) is a 52 kD membrane bound G protein-coupled receptor, and is expressed on neutrophils, monocytes, basophils, eosinophils, hepatocytes, lung smooth muscle and endothelial cells, and renal glomerular tissues (Van-Epps, D. E. et al., *J. Immunol.* 132: 2862-2867 (1984); Haviland, D. L. et al., *J. Immunol.* 154:1861-1869 (1995); Wetsel, R. A., *Immunol. Lett.* 44: 183-187 (1995); Buchner, R. R. et al., *J. Immunol.* 155: 308-315 (1995); Chenoweth, D. E. et al., *Proc. Natl. Acad. Sci.* 75: 3943-3947 (1978); Zwimer, J. et al., *Mol. Immunol.* 36:877-884 (1999)). The ligand-binding site of C5aR is complex and consists of at least two physically separable binding domains. One binds the C5a amino terminus (amino acids 1-20) and disulfide-linked core (amino acids 21-61), while the second binds the C5a carboxy-terminal end (amino acids 62-74) (Wetsel, R. A., *Curr. Opin. Immunol.* 7: 48-53 (1995)).

Only recently have non-peptide based C5a receptor antagonists been described in the literature (e.g., Sumichika, H., et al., *J. Biol. Chem.* (2002), 277, 49403-49407). Non-peptide based C5a receptor antagonist have been reported as being effective for treating endotoxic shock in rats (Stracham, A. J., et al., *J. of Immunol.* (2000), 164(12): 6560-6565); and for treating IBD in a rat model (Woodruff, T. M., et al., *J of Immunol.*, 2003, 171: 5514-5520). Non-peptide based C5a receptor modulators also have been described in the patent literature by Neurogen Corporation, (e.g., WO2004/043925, WO2004/018460, WO2005/007087, WO03/082826, WO03/08828, WO02/49993, WO03/084524); Dompe S. P. A. (WO02/029187); and The University of Queenland (WO2004/100975).

More recently, compounds having activity as C5aR antagonists have been identified and described in U.S. Pat. No. 8,445,515 B2. In general, the compounds are represented by formula A, while selected embodiments are described as having formula B:

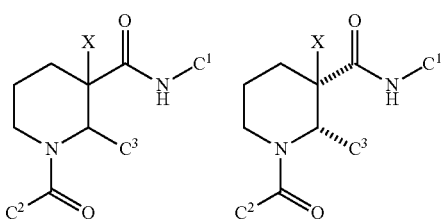

Selected compounds described therein are particularly active when resolved to their (2R,3S) isomers and are provided as:

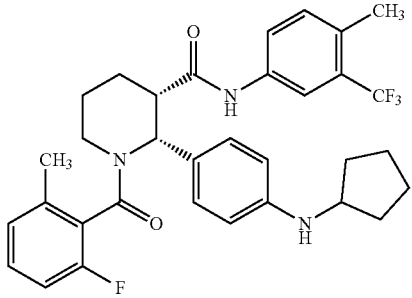

IA

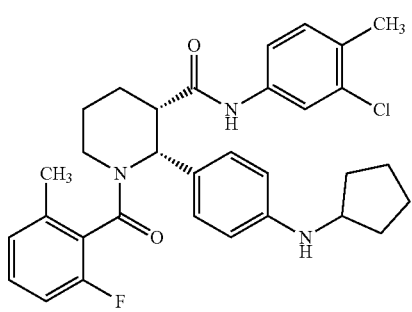

IB

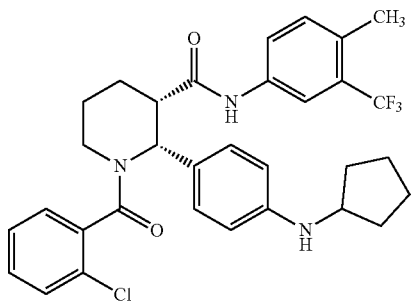

IC

The preparation of compound IA has been provided as shown in FIG. 4, and involves a lengthy synthesis including a classical resolution of isomers (see, for example, the conversion of 6 to 7).

There exists a need in the art for more efficient methods of preparation of compounds IA, IB and IC. The present disclosure provides such methods, as well as intermediates in the synthetic pathways.

BRIEF SUMMARY OF THE INVENTION

In one aspect, provided herein is a compound useful in the preparation of several C5aR antagonists, having the formula (i-3):

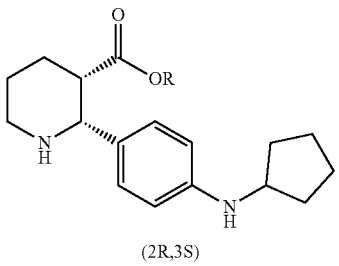

(i-3)

(2R,3S)

wherein R is selected from H, $C_{1-8}$ alkyl, aryl and aryl-$C_{1-4}$ alkyl, or a salt thereof, which is substantially free of enantiomeric or diastereomeric impurities (the (2R,3R), (2S,3R) and (2S,3S) isomers).

In another aspect, provided herein is a compound useful in the preparation of several C5aR antagonists, the compound having the formula (ii-4):

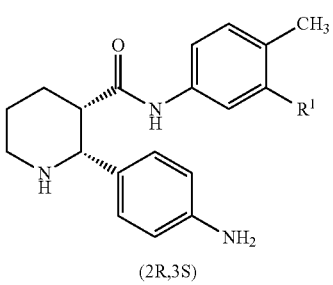

(ii-4)

(2R,3S)

or a salt thereof, wherein $R^1$ is Cl or $CF_3$, and wherein the compound is substantially free of enantiomeric or diastereomeric impurities (the corresponding (2R,3R), (2S,3R) and (2S,3S) isomers).

In yet another aspect, provided herein is a method of preparing a compound having formula (I):

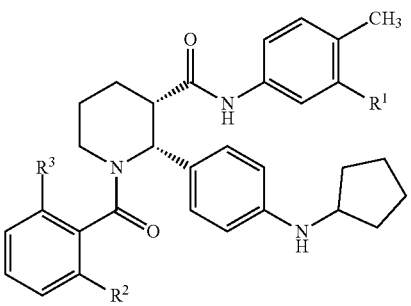

(I)

or a salt thereof, wherein $R^1$ is Cl or $CF_3$; $R^2$ is F or Cl; and $R^3$ is H or $CH_3$; and wherein said compound of formula (I) is substantially free of enantiomeric or diastereomeric impurities, the method comprising:

(a) contacting a compound having the formula (i-3):

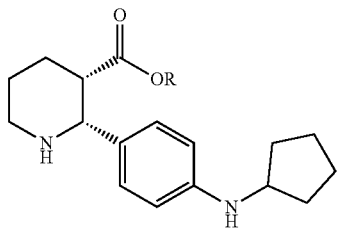
(i-3)

wherein R is selected from $C_{1-8}$ alkyl, aryl and aryl-$C_{1-4}$ alkyl, which is substantially free of enantiomeric or diastereomeric impurities, or a salt thereof, with a compound having the formula:

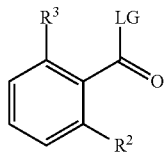

wherein LG is a leaving group; under conditions sufficient to form a compound of formula (i-4):

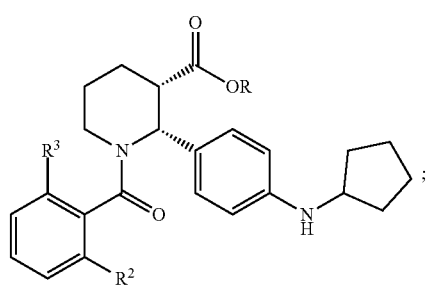
(i-4)

and
(b) converting the compound of formula (i-4) to said compound of formula (I) wherein said compound of formula (I) is substantially free of enantiomeric or diastereomeric impurities.

In still another aspect, provided herein is another method of preparing a compound having formula (I):

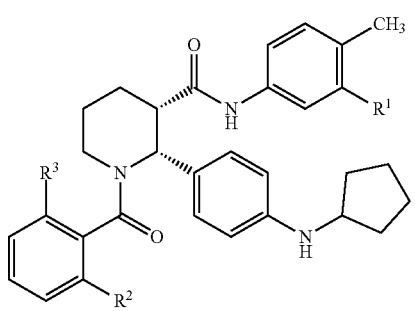
(I)

or a salt thereof, wherein $R^1$ is Cl or $CF_3$; $R^2$ is F or Cl; and $R^3$ is H or $CH_3$; and wherein the compound of formula (I) is substantially free of enantiomeric or diastereomeric impurities, the method comprising:
(a) contacting a compound having the formula (ii-4):

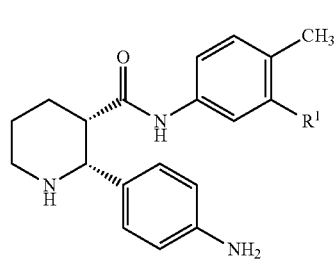
(ii-4)

or a salt thereof, said compound being substantially free of enantiomeric or diastereomeric impurities, with cyclopentanone and a reducing agent under conditions sufficient to form a compound having the formula (ii-5):

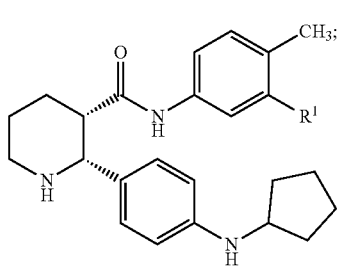
(ii-5)

and
(b) contacting said compound of formula (ii-5) with a compound having the formula:

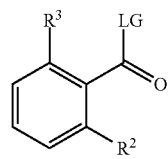

wherein LG is a leaving group; under conditions sufficient to form a compound of formula (I) which is substantially free of enantiomeric or diastereomeric impurities.

Still other processes are provided as described below having two, three, or four or more synthetic transformations resulting in the preparation of compounds IA, IB and/or IC, or their pharmaceutically acceptable salts.

DETAILED DESCRIPTION OF THE INVENTION

Definitions

Figure 1:
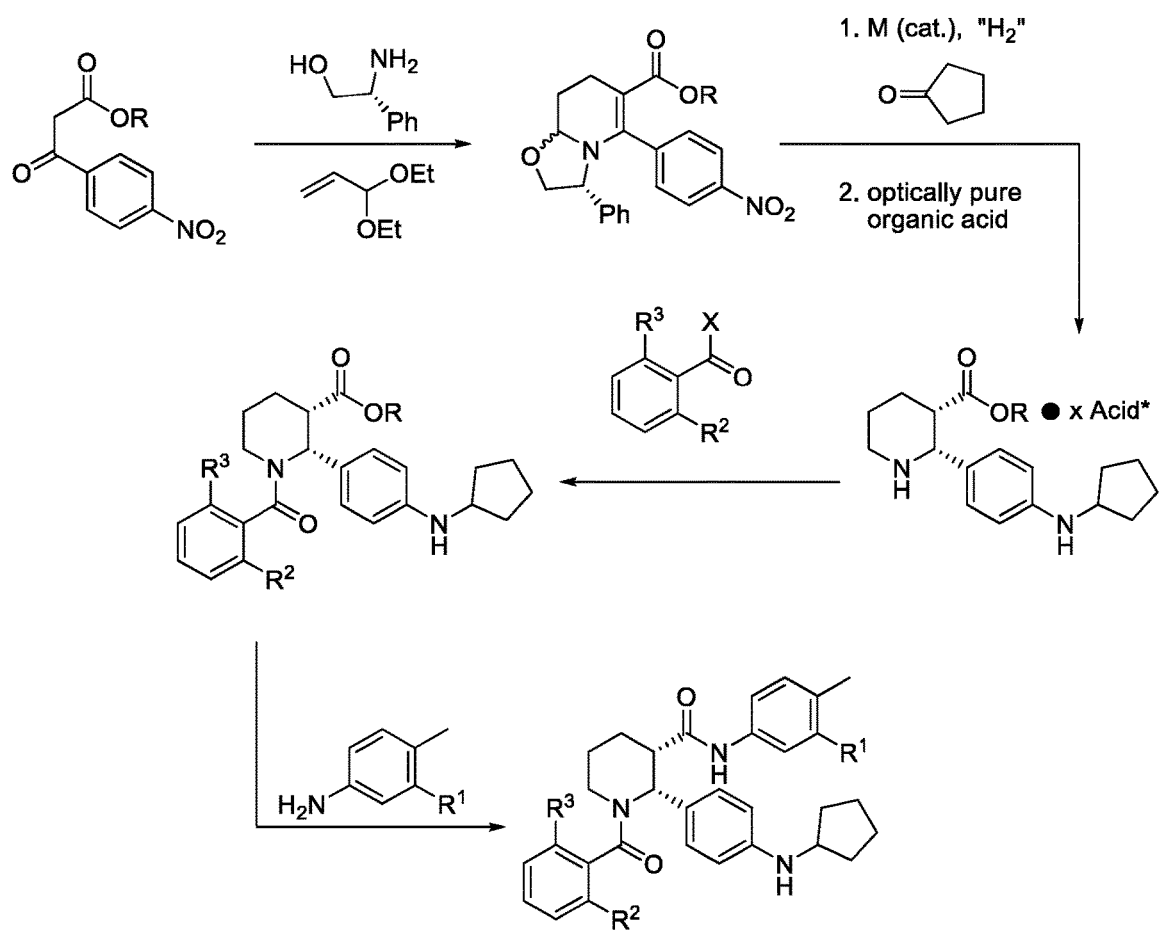
FIG. 1 provides a scheme generally illustrating the steps useful in preparation compounds IA, IB and IC, utilizing a hydrogenation step to set the (2R,3S) stereochemistry, followed by a reductive amination of cyclopentanone, benzoylation of the piperidine nitrogen, and addition of an aniline to form the C3 amide.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl. Substituents for the above noted aryl ring systems are selected from the group of acceptable substituents described below.

The term "arylalkyl" or "aryl-$C_{1-4}$ alkyl" is meant to include those radicals in which an aryl group is attached to an alkyl group (e.g., benzyl, phenethyl, and the like).

The above terms (e.g., "alkyl," and "aryl"), in some embodiments, will recite both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C (NH$_2$)=NR', —S(O)R', —S(O)$_2$R', —S(O)$_2$NR'R", —NR'S (O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$) =NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_{1}$-$C_{4}$)alkoxy, and perfluoro($C_{1}$-$C_{4}$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, a wavy line, "〜", that intersects a single, double or triple bond in any chemical structure depicted herein, represent the point attachment of the single, double, or triple bond to the remainder of the molecule.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

The term "under conditions sufficient to" refers to the selection of reaction conditions (including solvents or mixtures of solvents, temperature selection including a change in temperature as a reaction progresses, concentration of reactants, order of addition of reagents and reactants to a reaction mixture, length of time for reaction, etc.) which can bring about the desired reaction or transformation of one molecule to another.

"Converting" refers to carrying out a transformation on a compound to change the compound to a different compound, such as by modifying one functional group to another functional group, joining of two molecules to form a new molecule, or in some instances salt formation. However, 'converting' can also involve more than one transformation.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, diethyl ether, acetone, ethyl acetate, dimethylformamide, acetonitrile and dimethyl sulfoxide. Representative non-polar solvents include alkanes (pentanes, hexanes, etc.), cycloalkanes (cyclopentane, cyclohexane, etc.), benzene, toluene, and 1,4-dioxane.

"Reducing agent" refers to an agent capable of reducing an atom from a higher oxidation state to a lower oxidation state. Reducing agents can include, but are not limited to, zinc, iron, Raney nickel, platinum, iridium, rhodium, palladium, sodium sulfide, sodium dithionite, ammonium sulfide, and hydrogen donors such as lithium aluminum hydride, sodium borohydride and sodiumtriacetoxyborohydride.

"Leaving group" refers to groups that maintain the bonding electron pair during heterolytic bond cleavage. For example, a leaving group is readily displaced during a nucleophilic displacement reaction. Suitable leaving groups include, but are not limited to, chloro, bromo, iodo, hydroxyl, methanesulfonate (or mesylate), trifluoromethanesulfonate (triflate), benzenesulfonate, 4-methylbenzenesulfonate (tosylate), 4-nitrobenzenesulfonate, 4-chlorobenzenesulfonate, and the carboxylate component of a mixed or symmetrical anhydride. One of skill in the art will recognize other leaving groups useful in the present invention.

"Substantially free of enantiomeric or diastereomeric impurities" refers to a compound having at least one chiral center that is present as a single enantiomer or diastereomer in an amount of at least 80% relative to other enantiomers or diastereomers of the compound. In some embodiments, the term will refer to a compound that is present as a single enantiomer or diastereomer in an amount of at least 90%, 95%, 96%, 97%, 98%, 99%, or 99.5% relative to other enantiomers or diastereomers of the compound.

"Nitration agent" refers to a reagent capable of adding a nitro group, —$NO_2$, to a compound. Representative nitration agents include, but are not limited to, nitric acid.

"Chlorination agent" refers to a reagent capable of adding a chloro group, —Cl, to a compound. Representative chlorination agents include, but are not limited to, phosphorous oxychloride, thionyl chloride, oxalyl chloride and sulfuryl chloride.

The term "pharmaceutically acceptable salts" or "salts" is meant to include salts of the compounds which are prepared with relatively nontoxic acids or bases, depending on the particular substituents found on the compounds described herein. When compounds contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethyl enediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which may be in a co-crystal form. Co-crystals are those complexes of the compounds described herein wherein the compound is crystallized in the presence of a second compound such as an amino acid, a glycol, or a lower alcohol.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention, unless otherwise stated. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

"Kilogram scale" refers to a reaction performed where at least one of the reagents used is in an amount of at least 1 kilogram.

General

As noted above, provided herein are intermediates and processes useful in preparing C5aR antagonist compounds that are useful in treating diseases or disorders generally characterized as inflammatory diseases or disorders, cardiovascular or cerebrovascular diseases or disorders and autoimmune diseases or disorders.

Particular intermediates having a (2R,3S) configuration can be prepared according to methods herein, and subsequently converted to the C5aR antagonist compounds.

EMBODIMENTS OF THE INVENTION

C5aR Antagonist Intermediates

In one aspect, provided herein is a compound useful in the preparation of several C5aR antagonists, the compound having the formula (i-3):

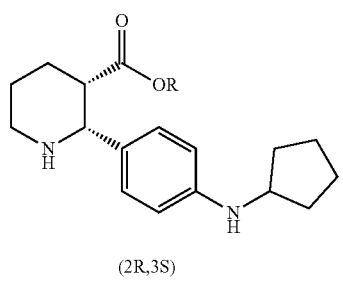

(2R,3S)

wherein R is selected from H, $C_{1-8}$ alkyl, aryl and aryl-$C_{1-4}$ alkyl, or a salt thereof. In one group of embodiments, the compound is substantially free of enantiomeric or diastereomeric impurities. In another group of embodiments, the compound (i-3) is provided as a L-DTTA salt ((−)-O,O'-di-p-toluoyl-L-tartaric acid salt); and in some embodiments the compound (i-3) is provided as a bis L-DTTA salt.

A compound of formula (i-3) which is substantially free of enantiomeric or diastereomeric impurities, refers to the compound which is substantially free of one or more of the following isomers (or any salt forms thereof):

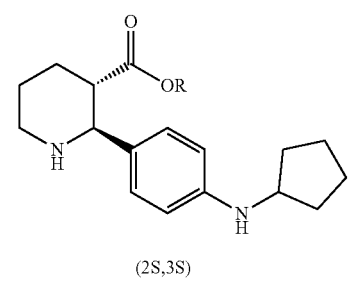

(2S,3S)

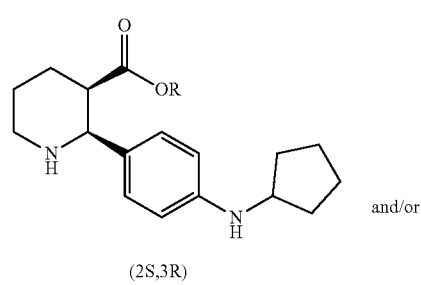

(2S,3R)

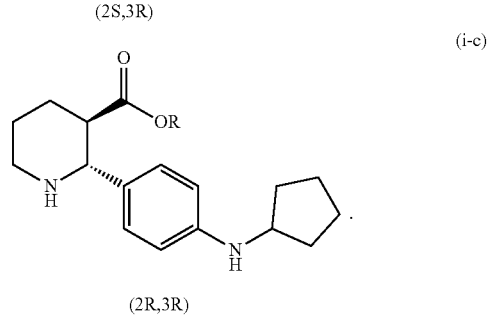

(2R,3R)

As provided herein, the total amount of any one of (i-a), (i-b) or (i-c) is typically less than about 5% by weight relative to the combined weights of (i-3), (i-a), (i-b) and (i-c). More typically, the amount of any combination of (i-a), (i-b) and/or (i-c) is less than about 5%, less than about 4%, less than about 3%, and in some embodiments is less than about 2.5, 2.0, 1.5 or 1.0% on a weight basis relative to (i-3).

In another aspect, provided herein is a compound useful in the preparation of several C5aR antagonists, the compound having the formula (ii-4):

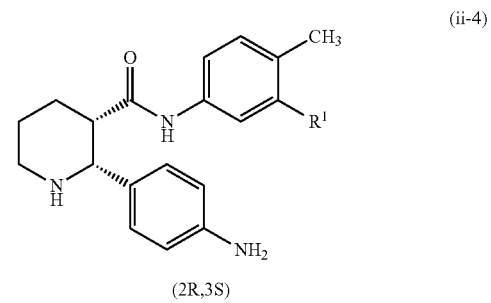

(2R,3S)

or a salt thereof, wherein $R^1$ is Cl or $CF_3$. In one group of embodiments, the compound is substantially free of enantiomeric or diastereomeric impurities. In another group of embodiments, the compound (ii-4) is provided as a L-DTTA salt ((−)-O,O'-di-p-toluoyl-L-tartaric acid salt); and in some embodiments, compound (ii-4) is provided as a bis L-DTTA salt.

A compound of formula (ii-4) which is substantially free of enantiomeric or diastereomeric impurities, refers to the compound which is substantially free of one or more of the following isomers (or any salt forms thereof):

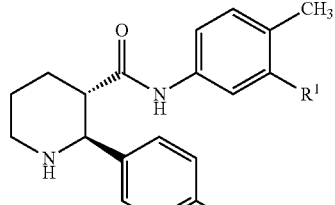

(ii-a)

(2S,3S)

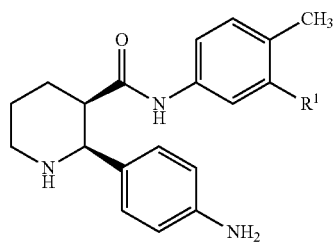

(ii-b)

and/or (2S,3R)

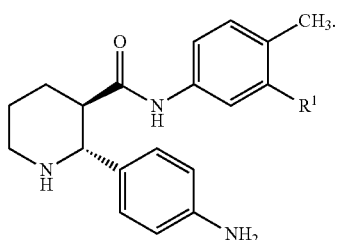

(ii-c)

(2R,3R)

As provided herein, the total amount of any one of (ii-a), (ii-b) or (ii-c) is typically less than about 5% by weight relative to the combined weights of (ii-4), (ii-a), (ii-b) and (ii-c). More typically, the amount of any combination of (ii-a), (ii-b) and/or (ii-c) is less than about 5%, less than about 4%, less than about 3%, and in some embodiments is less than about 2.5, 2.0, 1.5 or 1.0% on a weight basis relative to (ii-4).

Processes for the Preparation of C5aR Antagonists

In another aspect, provided herein is a method of preparing a compound having formula (I):

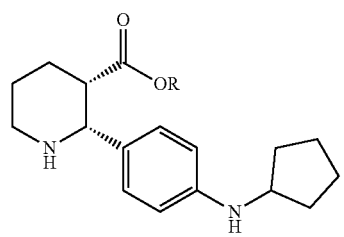

(I)

or a salt thereof, wherein $R^1$ is Cl or $CF_3$; $R^2$ is F or Cl; and $R^3$ is H or $CH_3$; and wherein said compound of formula (I) is substantially free of enantiomeric or diastereomeric impurities, the method comprising:

(a) contacting a compound having the formula (i-3):

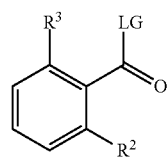

(i-3)

wherein R is selected from $C_{1-8}$ alkyl, aryl and aryl-$C_{1-4}$ alkyl, or a salt thereof, which is substantially free of enantiomeric or diastereomeric impurities, with a compound having the formula:

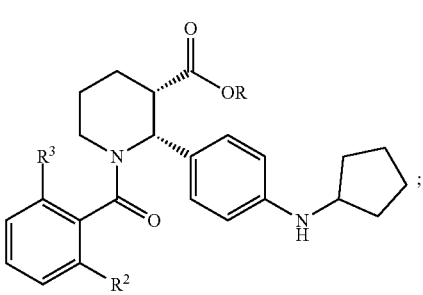

wherein LG is a leaving group; under conditions sufficient to form a compound of formula (i-4):

(i-4)

and (b) converting the compound of formula (i-4) to said compound of formula (I) wherein said compound of formula (I) is substantially free of enantiomeric or diastereomeric impurities.

Turning first to step (a), in one group of embodiments, a compound of formula (i-3) is provided which is substantially free of isomers (i-a), (i-b) and (i-c). In certain preferred embodiments, compound (i-3) is provided and is at least 95% pure, more preferably at least 96%, 97% or at least 98% pure, relative to the other isomers. In even further preferred embodiments, compound (i-3) is provided and is at least 99% or 99.5% pure, relative to the other isomers.

In step (a), compound (i-3) is contacted with a compound having the formula:

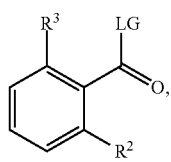

wherein LG is a leaving group. One of skill in the art will appreciate that a suitable leaving group is one that facilitates participation of the compound in the desired amide bond formation. More particularly, LG is a leaving group that facilitates reaction at the carbonyl center which bears LG. In one group of embodiments LG is a halogen. In another group of embodiments, LG is Cl. In yet another group of embodiments, -LG is selected from —OH, —OAc, —O—S(O)$_2$-(4-tolyl) and —O—S(O)$_2$methyl. In yet another group of embodiments, -LG is —OC(O)Ph(R$^2$)(R$^3$)—forming a symmetrical anhydride with the remainder of the molecule. In some embodiments, the contacting is carried out in an organic solvent or solvent mixture, or an aqueous solvent mixture—for example, a mixture of water and an ether such as methyl t-butyl ether (MTBE). In other embodiments, the solvent mixture is an aqueous THF, dioxane or acetonitrile solvent mixture. In still other embodiments, the contacting is carried out in the presence of a base. Suitable bases include triethylamine, N,N-diisopropylethylamine, DBU, and N-methyl morpholine, as well as potassium carbonate (K$_2$CO$_3$), potassium bicarbonate (KHCO$_3$), sodium carbonate (Na$_2$CO$_3$) or sodium bicarbonate (NaHCO$_3$). In one group of embodiments, the contacting is carried out at temperatures of from −20° C. to about 50° C. In another group of embodiments, the contacting is carried out at ambient temperature (about 25° C.±5° C.). After the initial contacting the reaction can be monitored until complete, which depending on the specific conditions (and solvents) used might involve a period of from about 20 minutes to about 3 days. Generally, the production of compound (i-4) is completed in about 1-2 hours. In some embodiments, compound (i-4) is isolated according to standard protocols such as those provided in the Examples below.

Compound (i-4) can then be converted to the compound of formula (I) via either direct amidation on the ester (present in (i-4)) or by first converting the ester to a carboxylic acid, followed by formation of the amide using a suitable aniline. As provided herein, a suitable aniline is selected from the group consisting of 4-methyl-3-(trifluoromethyl)aniline and 3-chloro-4-methylaniline.

For direct amidation, the aniline is generally combined with compound (i-4) in the presence of a metal reagent such as organoaluminum reagents or aluminum compounds (salts), alkyllithium compounds, Grignard reagents, organozinc reagents or zinc compounds (salts), sodium hydride, or sodium, potassium or lithium HMDS salts. In some embodiments, the metal reagent in an organoaluminum reagent, such as Al(Me)$_3$ or DABAL-Me$_3$ (a trimethylaluminum complex with DABCO). In some selected embodiments, the metal reagent is Al(Me)$_3$.

For those embodiments in which the ester form of compound (i-4) is converted to a carboxylic acid, the hydrolysis can take place utilizing an aqueous solution of an acid such as sulfuric acid. In some embodiments, temperatures above ambient temperature, for example up to 100° C. can be used. Coupling of the carboxylic acid form of (i-4) with an aniline, for example, 4-methyl-3-(trifluoromethyl)aniline or 3-chloro-4-methylaniline, can take place either via an activated ester method (using methanesulfonyl chloride with a base such as N,N-diisopropylethylamine) or another coupling reagent such as HATU with a base such as N-methylmorpholine.

In another aspect, provided herein is another method of preparing a compound having formula (I):

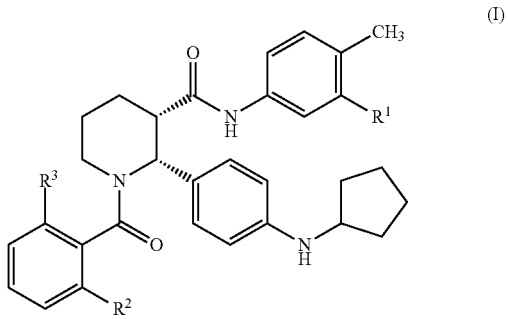

or a salt thereof, wherein R$^1$ is Cl or CF$_3$; R$^2$ is F or Cl; and R$^3$ is H or CH$_3$; and wherein the compound of formula (I) is substantially free of enantiomeric or diastereomeric impurities, the method comprising:

(a) contacting a compound having the formula (ii-4):

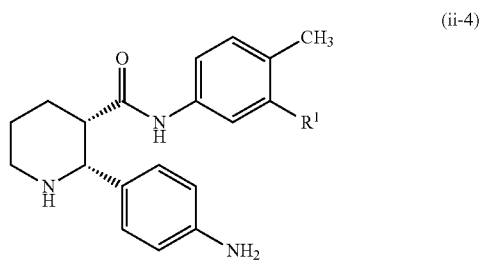

or a salt thereof, said compound being substantially free of enantiomeric or diastereomeric impurities, with cyclopentanone and a reducing agent under conditions sufficient to form a compound having the formula (ii-5):

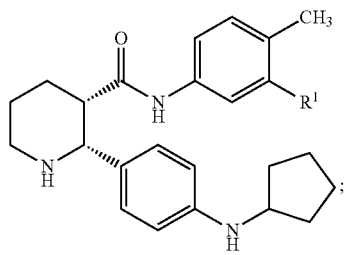

(ii-5)

and (b) contacting said compound of formula (ii-5) with a compound having the formula:

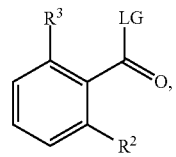

wherein LG is a leaving group; under conditions sufficient to form a compound of formula (I) which is substantially free of enantiomeric or diastereomeric impurities In one group of embodiments, $R^1$ is $CF_3$; $R^2$ is F; and $R^3$ is $CH_3$. In another group of embodiments, $R^1$ is $CF_3$; $R^2$ is Cl; and $R^3$ is H. In yet another group of embodiments, $R^1$ is Cl; $R^2$ is F; and $R^3$ is $CH_3$.

Turning first to step (a), in one group of embodiments, a compound of formula (ii-4) is provided which is substantially free of isomers (ii-a), (ii-b) and (ii-c). In certain preferred embodiments, compound (ii-4) is provided and is at least 95% pure, more preferably at least 96%, 97% or at least 98% pure, relative to the other isomers. In even further preferred embodiments, compound (ii-4) is provided and is at least 99% or 99.5% pure, relative to the other isomers.

Compound (ii-4) is generally first contacted with cyclopentanone and an acid to facilitate formation of an intermediate imine, which is then reduced to the corresponding amine using a suitable reducing agent. Examples of suitable reducing agents include hydrogen gas (with a palladium or other metal catalyst), borohydride reagents and aluminum hydride reagents. In one group of embodiments, the reducing agents are borohydride reagents, such as sodium or lithium borohydride, sodium cyanoborohydride, or sodium triacetoxyborohydride. Conditions for both the imine formation and subsequent reduction can be varied according to conventional methods. For example, imine formation can be accomplished in a single solvent, or a solvent mixture (such as dichloromethane and p-dioxane). Similarly, the temperature for the reactions will be selected to reduce the amounts of side products and maintain a good yield. Generally, such reactions can be carried out at ambient temperatures for periods of 1-2 hours up to 18 hours, or more.

The compound of formula (ii-5) can be isolated using standard work up conditions for a reductive amination procedure. Such conditions can include, for example, neutralizing any acid in the reaction (or contacting) mixture and separating the compound (ii-5) by extracting the mixture with an organic solvent and then removing solvent from the organic portions. Typically, further purification of compound (ii-5) is not necessary before initiating step (b).

In step (b), the product of step (a) is contacted with a compound having the formula:

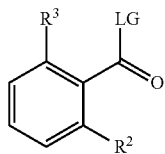

wherein LG is a leaving group. As with the earlier method described, one of skill in the art will appreciate that a suitable leaving group is one that facilitates participation of the compound in the desired amide bond formation. More particularly, LG is a leaving group that facilitates reaction at the carbonyl center which bears LG. In one group of embodiments LG is a halogen. In another group of embodiments LG is Cl. In yet another group of embodiments, -LG is selected from —OH, —OAc, —O—S(O)$_2$-(4-tolyl) and —O—S(O)$_2$methyl. In yet another group of embodiments, -LG is —OC(O)Ph($R^2$)($R^3$)—forming a symmetrical anhydride with the remainder of the molecule. In some embodiments, the contacting is carried out in an organic solvent or solvent mixture, or an aqueous solvent mixture—for example, a mixture of water and an ether such as methyl t-butyl ether (MTBE). In selected embodiments, the solvent is an organic solvent such as THF or another ether solvent. In still other embodiments, the contacting is carried out in the presence of a base. Suitable bases include triethylamine, diisopropyl ethyl amine, DBU, and N-methyl morpholine, as well as potassium carbonate ($K_2CO_3$), potassium bicarbonate ($KHCO_3$), sodium carbonate ($Na_2CO_3$) or sodium bicarbonate ($NaHCO_3$). In one group of embodiments, the contacting is carried out at temperatures of from −20° C. to about 50° C. In another group of embodiments, the contacting is carried out at ambient temperature (about 25° C.±5° C.). After the initial contacting the reaction can be monitored until complete, which depending on the specific conditions (and solvents) used might involve a period of from about 20 minutes to about 3 days. Generally, the production of compound (I) is completed in about 1-2 hours. In some embodiments, the compound of formula (I) is isolated according to standard protocols such as those provided in the Examples below.

In yet another aspect, provided herein are processes for the preparation of compounds of formula (I), or a pharmaceutically acceptable salt, solvate, hydrate or rotamer thereof, comprising any two, three or four of the steps (a), (b), (c), (d), (d1) and (d2), which steps can be contiguous in the synthetic scheme or non-contiguous:

(a) reacting an ester (R is alkyl, preferably $C_{1-8}$ alkyl, or aryl or aryl-$C_{1-4}$ alkyl) of 3-(4-nitrophenyl)-3-oxo-propanoate (i-1), (R)-(−)-2-phenylglycinol, and acrolein diethyl acetal or an equivalent thereof, to produce compound (i-2);

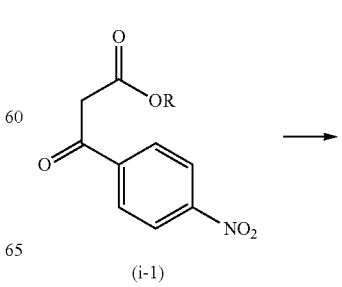

(i-1)

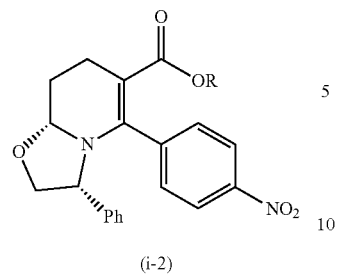

(i-2)

(b) hydrogenating or reducing and (i-2) to produce an intermediate amine and converting the intermediate to (i-3) with cyclopentanone and a reducing agent;

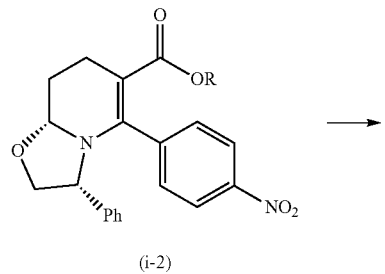

(i-2)

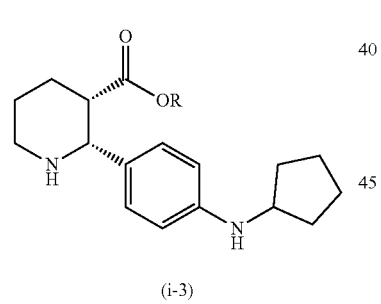

(i-3)

(c) combining (i-3) with either 2-fluoro-6-methylbenzoyl chloride or 2-chlorobenzoyl chloride to provide (i-4);

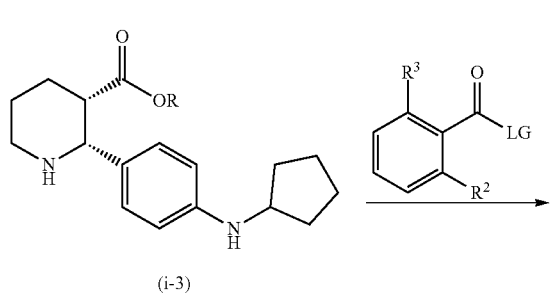

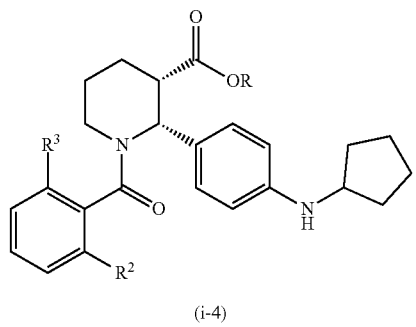

(i-4)

(d) combining (i-4) with 3-chloro-4-methylaniline or 3-tri-fluoromethyl-4-methylaniline under conditions sufficient to provide a compound of formula (I).

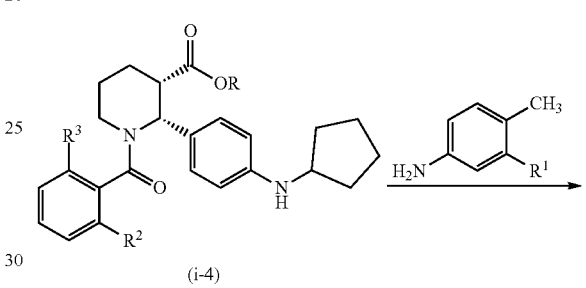

(i-4)

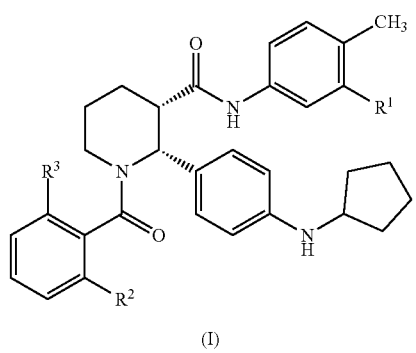

(I)

Optionally, in some embodiments, the transformation provided in step (d) can be conducted in a two-step process, involving:

(d)(1) conversion of the ester (i-4) to a carboxylic acid (i-5):

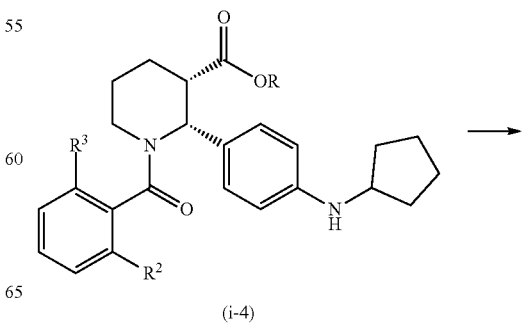

(i-4)

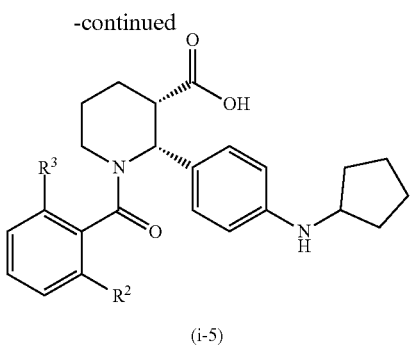

(i-5)

(d)(2) combining (i-5) with 3-chloro-4-methylaniline or 3-trifluoromethyl-4-methylaniline under conditions sufficient to provide a compound of formula (I).

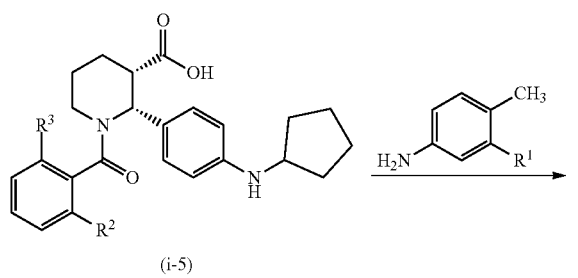

(I)

In some embodiments, the process of preparing compounds of formula (I) comprises steps (a) and (b). In other embodiments, the process of preparing compounds of formula (I) comprises steps (b) and (c). In yet other embodiments, the process of preparing compounds of formula (I) comprises steps (c) and (d). In still other embodiments, the process of preparing compounds of formula (I) comprises steps (c) and (d)(1). In other embodiments, the process of preparing compounds of formula (I) comprises steps (c) and (d)(2). In still other embodiments, the process of preparing compounds of formula (I) comprises steps (b) and (d). In yet other embodiments, the process of preparing compounds of formula (I) comprises steps (b) and (d1). In other embodiments, the process of preparing compounds of formula (I) comprises steps (b) and (d2).

In some embodiments, the process of preparing compounds of formula (I) comprises steps (a) and (c). In other embodiments, the process of preparing compounds of formula (I) comprises steps (a) and (d). In yet other embodiments, the process of preparing compounds of formula (I) comprises steps (a) and (d1). In still other embodiments, the process of preparing compounds of formula (I) comprises steps (a) and (d2).

In other embodiments, the process of preparing compounds of formula (I) comprises at least three of steps (a), (b), (c), and (d), or optionally (d)(1) and (d)(2). In still other embodiments, the process of preparing compounds of formula (I) comprises steps (a), (b) and (c). In other embodiments, the process of preparing compounds of formula (I) comprises steps (a), (b) and (d). In yet other embodiments, the process of preparing compounds of formula (I) comprises steps (a), (b) and (d1). In other embodiments, the process of preparing compounds of formula (I) comprises steps (a), (b) and (d2). In another group of embodiments, the process of preparing compounds of formula (I) comprises steps (b), (c) and (d). In yet other embodiments, the process of preparing compounds of formula (I) comprises steps (b), (c) and (d1). In other embodiments, the process of preparing compounds of formula (I) comprises steps (b), (c) and (d2).

In yet another related aspect, provided herein are processes for the preparation of compounds of formula (I), or a pharmaceutically acceptable salt, solvate, hydrate or rotamer thereof, comprising any two, three or four of the steps (a'), (b'), (c'), (d') and (e'), which steps can be contiguous in the overall synthetic pathway, or non-contiguous:

(a') reacting an ester (R is alkyl, preferably $C_{1-8}$ alkyl, aryl or aryl-$C_{1-4}$ alkyl) of 3-(4-nitrophenyl)-3-oxo-propanoate (i-1, or ii-1, wherein R is alkyl) with 3-chloro-4-methylaniline or 3-trifluoromethyl-4-methylaniline under conditions sufficient to provide a compound of formula (ii-2);

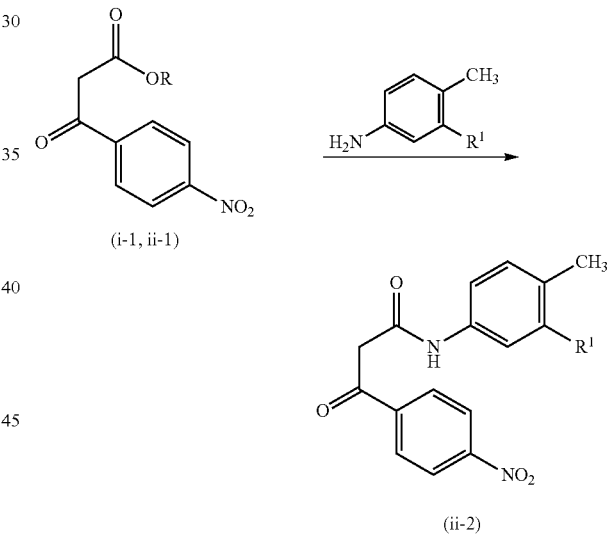

(b') reacting (ii-2), (R)-(−)-2-phenylglycinol, and acrolein diethyl acetal or an equivalent thereof, to produce compound (ii-3);

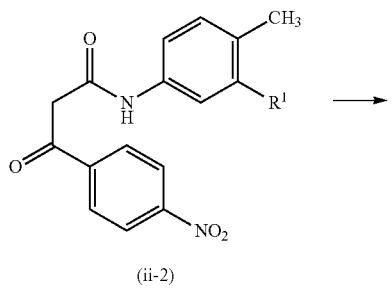

(ii-2)

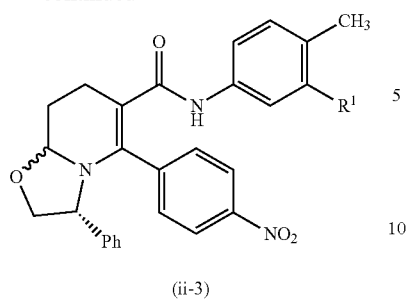

(ii-3)

(c') reducing (ii-3) under conditions sufficient to produce an intermediate diamine (ii-4) that is substantially free of enantiomeric or diastereomeric impurities;

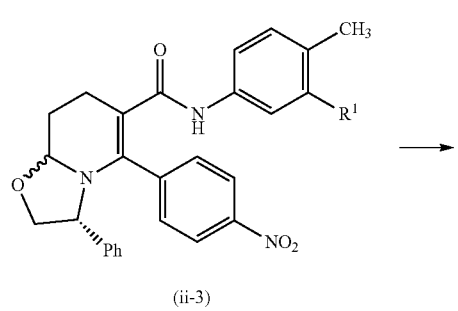

(ii-3)

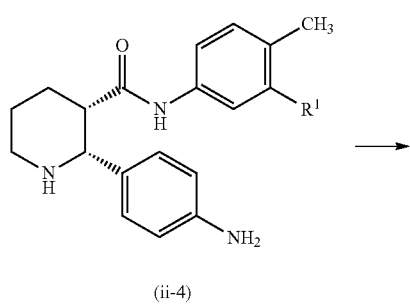

(ii-4)

(d') converting (ii-4) to (ii-5) with cyclopentanone and a reducing agent; and

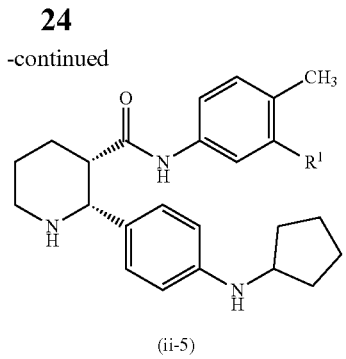

(ii-5)

(e') combining (ii-5) with either 2-fluoro-6-methylbenzoyl chloride or 2-chlorobenzoyl chloride to provide (I);

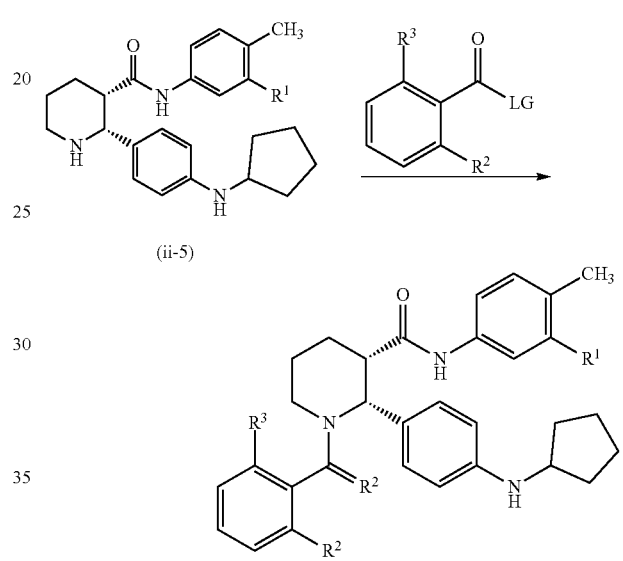

(I)

In the processes above using any of steps (a), (b), (c), (d), (d1), (d2), (a'), (b'), (c'), (d'), or (e'), one of skill in the art will understand that the indicated compounds can be used, in some instances, as a salt, hydrate or solvate form; and that conditions can be selected that facilitate the indicated reaction and to increase the yield of the step's product and/or the purity of the step's product.

In some embodiments, the process of preparing compounds of formula (I) comprises steps (a') and (b'). In other embodiments, the process of preparing compounds of formula (I) comprises steps (b') and (c'). In yet other embodiments, the process of preparing compounds of formula (I) comprises steps (c') and (d'). In still other embodiments, the process of preparing compounds of formula (I) comprises steps (d') and (e').

In some embodiments, the process of preparing compounds of formula (I) comprises steps (a') and (c'). In still other embodiments, the process of preparing compounds of formula (I) comprises steps (a') and (d'). In yet other embodiments, the process of preparing compounds of formula (I) comprises steps (a') and (e').

In other embodiments, the process of preparing compounds of formula (I) comprises steps (b') and (d'). In other embodiments, the process of preparing compounds of formula (I) comprises steps (b') and (e'). In other embodiments, the process of preparing compounds of formula (I) comprises steps (c') and (e').

In some embodiments, the process of preparing compounds of formula (I) comprises steps (a'), (b') and (c'). In some embodiments, the process of preparing compounds of formula (I) comprises steps (a'), (b') and (d'). In some embodiments, the process of preparing compounds of formula (I) comprises steps (a'), (b') and (e'). In some embodiments, the process of preparing compounds of formula (I) comprises steps (a'), (c') and (d'). In some embodiments, the process of preparing compounds of formula (I) comprises steps (a'), (c') and (e'). In other embodiments, the process of preparing compounds of formula (I) comprises steps (a'), (d') and (e'). In yet other embodiments, the process of preparing compounds of formula (I) comprises steps (b'), (c') and (d'). In still other embodiments, the process of preparing compounds of formula (I) comprises steps (b'), (c') and (e'). In still other embodiments, the process of preparing compounds of formula (I) comprises steps (c'), (d') and (e').

In other embodiments, the process of preparing compounds of formula (I) comprises at least four of steps (a'), (b'), (c'), (d'), and (e'). In selected embodiments, the process of preparing compounds of formula (I) comprises steps (a'), (b'), (c') and (d'). In other embodiments, the process of preparing compounds of formula (I) comprises steps (a'), (b'), (c') and (e'). In yet other embodiments, the process of preparing compounds of formula (I) comprises steps (a'), (b'), (d') and (e'). In other embodiments, the process of preparing compounds of formula (I) comprises steps (a'), (c'), (d') and (e'). In another group of embodiments, the process of preparing compounds of formula (I) comprises steps (b'), (c'), (d') and (e'). In yet other embodiments, the process of preparing compounds of formula (I) comprises steps (a'), (b'), (c'), (d') and (e').

The processes provided above and herein, provide cost effective, safe, efficient, and/or readily scaleable processes useful for the large scale or commercial production of each of IA, IB and IC, or a pharmaceutically acceptable salt, solvate, hydrate, or rotamer thereof.

In one embodiment, provided herein are processes for the preparation of compounds of formula (I), or a pharmaceutically acceptable salt, solvate, hydrate, or rotamer thereof, that are substantially pure. In one embodiment, provided herein are processes for the preparation of compounds of formula (I), or a pharmaceutically acceptable salt, solvate, hydrate, or rotamer thereof, that are substantially chemically pure. In one embodiment, provided herein are processes for the preparation of compounds of formula (I), or a pharmaceutically acceptable salt, solvate, hydrate, or rotamer thereof, that is suitable for use in humans, such as for treating, preventing, and/or managing diseases or conditions, including but not limited to, diseases mediated by antagonists of the C5a receptor.

In one embodiment, provided herein are processes for the preparation of compounds of formula (I), or a pharmaceutically acceptable salt, solvate, hydrate, or rotamer thereof, on a scale of greater than 1 gram, greater than 10 gram, greater than 100 gram, greater than 1,000 gram, greater than 10,000 gram, or greater than 100,000 gram.

In one embodiment, provided herein are processes for the preparation of compounds of formula (I), or a pharmaceutically acceptable salt, solvate, hydrate, or rotamer thereof, in an overall yield of greater than about 10%, greater than about 15%, greater than about 20%, greater than about 25%, greater than about 30%, greater than about 40%, greater than about 50%, greater than about 60%, greater than about 70%, greater than about 80%, greater than about 90%, or greater than about 95%, wherein the yield is calculated based on the limiting starting material.

In one embodiment, provided herein are processes for the preparation of compounds of formula (I), or a pharmaceutically acceptable salt, solvate, hydrate, or rotamer thereof, that is substantially pure. In one embodiment, the purity of the compounds of formula IA, IB and IC, or a pharmaceutically acceptable salt, solvate, hydrate, or rotamer thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

In one embodiment, the total impurities in the compounds of formula IA, IB and/or IC, or a pharmaceutically acceptable salt, solvate, hydrate, or rotamer thereof, produced by a process provided herein, is less than about 5% w/w, less than about 4% w/w, less than about 3% w/w, less than about 2% w/w, less than about 1% w/w, less than about 0.5% w/w, less than about 0.2% w/w, less than about 0.1% w/w, less than about 0.05% w/w, less than about 0.02% w/w, less than about 0.01% w/w, less than about 0.005% w/w, or less than about 0.001% w/w relative to the total batch.

In one embodiment, an individual impurity in the compounds of formula (I), or a pharmaceutically acceptable salt, solvate, hydrate, or rotamer thereof, produced by a process provided herein, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, less than about 0.01% w/w, less than about 0.005% w/w, less than about 0.001% w/w, less than about 0.0005% w/w, or less than about 0.0001% w/w relative to the total batch.

In one embodiment, the processes provided herein compounds of formula (I), or a pharmaceutically acceptable salt, solvate, hydrate, or rotamer thereof, that is substantially chemically pure. In one embodiment, the chemical purity of the compound of formula IA, IB or IC, or a pharmaceutically acceptable salt, solvate, hydrate, or rotamer thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

In one embodiment, the purity profile of a reaction mixture or an isolated product of the processes provided herein is analyzed by one or more analytical method(s), such as, e.g., HPLC (high performance liquid chromatography), GC (gas chromatography), and TLC (thin layer chromatography). In one embodiment, an impurity is detectable by an analytical method, such as, e.g., HPLC, GC, or TLC. In one embodiment, the impurity or contemplated impurity in the reaction mixture or isolated product of the processes provided herein includes, but is not limited to, the starting material used in the reaction or any starting material used in the preceding steps.

In some instances, an impurity in an isolated product of the processes provided herein may be a volatile organic compound, such as, e.g., methanol, dimethylformamide, dichloromethane, toluene, acetone, methyl t-butyl ether, ethanol, or tetrahydrofuran.

In some instances, the weight loss on drying (LOD) of the compound of formula IA, IB or IC, or a pharmaceutically acceptable salt, solvate, hydrate, or rotamer thereof, produced by a process provided herein, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, or less than about 0.01% w/w relative to the total batch.

In one embodiment, the residue on ignition of the compound of formula IA, IB or IC, or a pharmaceutically acceptable salt, solvate, hydrate, or rotamer thereof, produced by a process provided herein, is less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, or less than about 0.01% w/w relative to the total batch.

In one embodiment, the total heavy-metal-based impurity in the compound of formula IA, IB or IC, or a pharmaceutically acceptable salt, solvate, hydrate, or rotamer thereof, produced by a process provided herein, is less than about 500 ppm (parts per million) w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w relative to the total batch.

In one embodiment, provided herein are processes for preparing the compound of formula IA, IB or IC, or a pharmaceutically acceptable salt, solvate, hydrate, or rotamer thereof, that is substantially free of one or more residual solvents, including but not limited to, methanol, ethanol, dimethylformamide, toluene, dichloromethane, acetone, methyl t-butyl ether, and tetrahydrofuran. In one embodiment, the residual solvent or the contemplated residual solvent is less than about 5,000 ppm w/w, less than about 2,000 ppm w/w, less than about 1,000 ppm w/w, less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w relative to the total batch. In one embedment, the contemplated residual solvent, such as, e.g., methanol, ethanol, dimethylformamide, toluene, dichloromethane, acetone, methyl t-butyl ether, and tetrahydrofuran, cannot be detected.

In one embodiment, provided herein are processes for preparing the compound of formula IA, IB or IC, or a pharmaceutically acceptable salt, solvate, hydrate, or rotamer thereof, that has a water content of less than about 5% w/w, less than about 4% w/w, less than about 3% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, or less than about 0.1% w/w relative to the total batch.

In one embodiment, provided herein are processes for preparing the compound of formula IA, IB or IC, or a pharmaceutically acceptable salt, solvate, hydrate, or rotamer thereof, that has the appearance of a white or off-white solid.

In one embodiment, one or more steps of the processes provided herein is carried out under GMP (Good Manufacturing Process) conditions. In one embodiment, one or more steps of the processes provided herein is carried under non-GMP conditions.

EXAMPLES

Abbreviations used in the examples below have the following meanings:

aq: aqueous; BBr$_3$: boron tribromide; CH$_2$Cl$_2$ or DCM: dichloromethane; CH$_3$CN: acetonitrile; CH$_3$OH or MeOH: methanol; DIEA: N,N-diisopropylethylamine; DMF: dimethyl formamide; DMSO: dimethyl sulfoxide; equiv. or eq.: equivalents; Et$_3$N: triethylamine; Et$_2$O: diethyl ether; EtOH: ethanol; h: hour(s); HATU, O-(7-Azabenzotriazol-1-yl)-N, N,N',N'-tetramethyluronium hexafluorophosphate; HCl: hydrogen chloride; H$_2$O: water; K$_2$CO$_3$: potassium carbonate; KHSO$_4$: potassium bisulfate; MgSO$_4$: magnesium sulfate; mL: milliliter; NaCl: sodium chloride; NaH: sodium hydride; NaHCO$_3$: sodium bicarbonate; NaOEt: sodium ethoxide; NaOH: sodium hydroxide; NaOMe: sodium methoxide; Na$_2$SO$_4$: sodium sulfate; NH$_4$Cl: ammonium chloride; NMP: N-methyl pyrrolidinone pH: −log [H$^+$]; POCl$_3$: phosphoryl trichloride; PPTS: pyridinium p-toluenesulfonate; RP-HPLC: reversed phase high pressure liquid chromatography; RT: room temperature; TFA: trifluoroacetic acid; THF: tetrahydrofuran; TLC: thin layer chromatography Example 1

This example illustrates the preparation of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide by the method provided more generally in FIG. 1 (Scheme 1) using the reagents provided below:

Route 1:

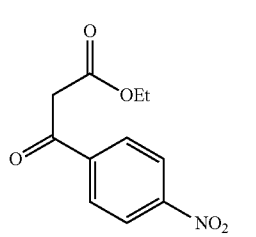 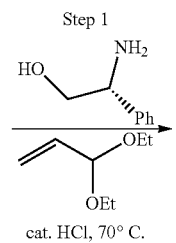 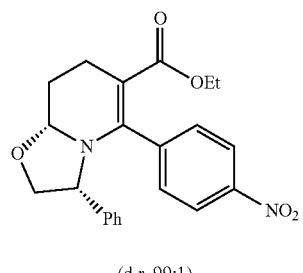 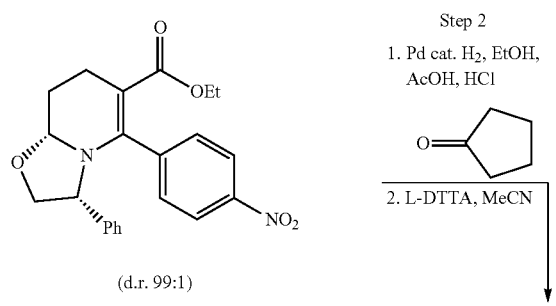

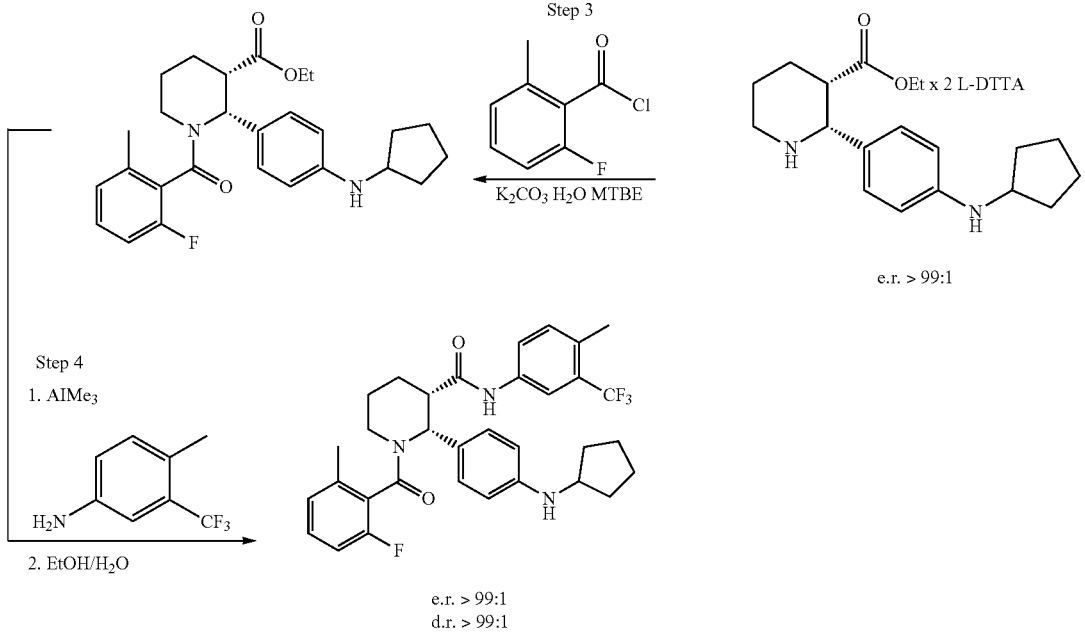

e.r. > 99:1
d.r. > 99:1

Step 1:

An oven-dried 12 L, 3-necked flask equipped with a mechanical stirrer, condenser, and thermometer was charged with acrolein diethyl acetal (1127 g, 8.666 mole, 1.05 equiv.) and warmed up to 40° C. A mixture of solid ethyl 3-(4-nitrophenyl)-3-oxo-propanoate (1956 g, 8.253 mole) and (R)-(−)-2-phenylglycinol (>99.5% e.e., 1187 g, 8.666 mole, 1.05 equiv.) was added in portions over 40 min. to maintain a stirrable mixture at an internal temperature of approximately 40° C. After all solids were added, the mixture was stirred at 40° C. for 10 minutes. 4M HCl in dioxane (206.2 mL, 0.825 mole, 10 mol. %) was subsequently added through the condenser within 2 minutes and the internal temperature was increased to 70° C. The reaction was stirred for 22 h whereupon LC-MS showed consumption of starting materials and enamine intermediate. The heating was turned off and ethanol (6.6 L) was added. The solution was then seeded with 4 g of ethyl (3R,8aR)-5-(4-nitrophenyl)-3-phenyl-3,7,8,8α-tetrahydro-2H-oxazolo[3,2-a]pyridine-6-carboxylate and stirred at room temperature for 18 h. The solid was subsequently filtered off and 0.1 L of ethanol was used to rinse the flask and equipment onto the filter. The isolated solid was then washed three times on the filter with ethanol (250 mL each) and dried under vacuum to generate 1253 g of ethyl (3R,8aR)-5-(4-nitrophenyl)-3-phenyl-3,7,8,8a-tetrahydro-2H-oxazolo[3,2-a]pyridine-6-carboxylate as a bright yellow solid (38% yield, 98.5% HPLC wt/wt purity, 0.15 wt % of EtOH).

Step 2:

260 g of ethyl (3R,8aR)-5-(4-nitrophenyl)-3-phenyl-3,7,8,8a-tetrahydro-2H-oxazolo[3,2-a]pyridine-6-carboxylate (0.659 mol), 0.66 L of ethanol, and 56 g of palladium catalyst (10% Pd/C, Degussa type E101 NE/W, 50% wet, 21.5 wt. % of powder, 4.0 mol % Pd) were placed in a 2.2 L Parr bottle and purged with nitrogen. The bottle was mounted on a Parr shaker apparatus and hydrogen was added at a rate to keep the external temperature of the bottle below 30° C. After 4 hours, the consumption of hydrogen slowed down. The bottle was then shaken under 50 psi of hydrogen for 2 hours. 94 mL of glacial acetic acid (1.65 mol, 2.5 equiv.) was subsequently added to the bottle and the bottle was purged three times with hydrogen at 50 psi. The bottle was then shaken under 35-55 psi of hydrogen for 48 hours, keeping the temperature below 30° C. The bottle was removed from the apparatus and 55 mL of 12M HCl aq. was added (0.659 mol, 1 equiv.) followed by 87 mL of cyclopentanone (0.989 mol, 1.5 equiv.). The bottle was purged three times with hydrogen at 50 psi and then shaken under 50 psi of hydrogen for 16-20 hours. The mixture was removed from the apparatus and filtered through a fritted funnel containing celite (80 g) and then washed three times with 0.125 L of ethanol. 54.1 g of anhydrous sodium acetate (0.659 mol, 1 equiv.) was added and the mixture was concentrated in vacuo at 40-55° C. to remove 0.9 L of the volatile components. 2.0 L of acetonitrile was added and 2.0 L of volatile components were removed in vacuo. The crude material was diluted with 1.0 L of acetonitrile and mechanically stirred at r.t. for 30 minutes. The mixture was filtered through Celite (40 g) and the cake was washed with 0.28 L of acetonitrile. The combined filtrates gave a solution of the crude amine acetate (Solution A, e.e.=78%). Solutions A of two independent runs were combined for further processing.

In a 12-L 3-neck flask equipped with a mechanical stirrer, internal thermometer, and reflux condenser (−)-O,O'-di-p-toluoyl-L-tartaric acid (1.019 kg, 2.64 mol, 2 equiv.) was dissolved in 5.8 L of acetonitrile. The mixture was heated to 60° C. with stirring, followed by a quick addition of 1 L of Solution A. The resultant solution was seeded with 4 g of the crystalline ethyl (2R,3S)-2-[4-(cyclopentylamino)phenyl]piperidine-3-carboxylate (−)-O,O'-di-p-toluoyl-L-tartaric acid salt (1:2) and stirred at 60° C. for 15 minutes. After 15 minutes at 60° C. the seed bed has formed. The remaining amount of Solution A was added over a period of 2.5 hours, maintaining an internal temperature at 60° C. When the addition was complete, the heat source was turned off and the mixture was stirred for 17 hours, reaching a final temperature of 22.5° C. The suspension was filtered and the solids were washed with 0.50 L of acetonitrile to rinse the equipment and transfer all solids onto the filter. The resultant wet solids were washed on the funnel with 3.0 L of acetonitrile and dried in a vacuum oven at 45° C. for 48 hours to provide 1.005 kg of ethyl (2R,3S)-2-[4-(cyclopentylamino)phenyl]piperidine-3-carboxylate (−)-O,O'-di-p-toluoyl-L-tartaric acid salt (1:2) as an off-white solid (70% yield, contains 1 wt. % of acetonitrile). The enantiomeric ratio of the product was 99.4:0.6.

Step 3:

In a 5 L 3-necked flask equipped with a mechanical stirrer and an addition funnel, solid anhydrous potassium carbonate ($K_2CO_3$, 226 g, 1.64 mol, 4.1 equiv.) was dissolved in $H_2O$ (0.82 L) and cooled to ambient temperature. MTBE (0.82 L) was added, followed by solid ethyl (2R,3S)-2-[4-(cyclopentylamino)phenyl]piperidine-3-carboxylate (−)-O,O'-di-p-toluoyl-L-tartaric acid salt (1:2) (436 g, 0.400 mol). The mixture was vigorously stirred at r.t. for 1 hour, then 2-fluoro-6-methylbenzoyl chloride (72.5 g, 0.420 mmol, 1.05 equiv.) in MTBE (0.14 L) was added dropwise over 1 hour. The product started precipitating from the reaction before addition of the acid chloride was completed. The reaction was vigorously stirred at r.t. for 30 minutes and monitored by LC-MS for the disappearance of starting material. The mixture was subsequently transferred to a 5 L evaporation flask using 0.3 L of MTBE to rinse the equipment and remove all solids. The mixture was concentrated in vacuo to remove the MTBE, then 0.3 L of heptane was added and the mixture was evaporated again to leave only the product suspended in aqueous solution. The flask was removed from the rotavap and water (0.82 L) and heptane (0.82 L) were added. The suspension was vigorously stirred for 16 hours using a mechanical stirrer. The contents were then filtered and the solid was washed with water (2×0.42 L) and heptane (0.42 L). The solid was dried in a vacuum oven at 45° C. to provide 172 g of ethyl (2R,3S)-2-[4-(cyclopentylamino)phenyl]-1-(2-fluoro-6-methyl-benzoyl)piperidine-3-carboxylate as an off-white powder (95% yield).

Step 4:

A 0.5 L 3-necked round-bottom flask was dried overnight in an oven at 200° C. and then cooled under a stream of nitrogen. The flask was equipped with a magnetic stir bar, nitrogen inlet, and a thermometer. The flask was charged with 30.2 g of ethyl (2R,3S)-2-[4-(cyclopentylamino)phenyl]-1-(2-fluoro-6-methyl-benzoyl)piperidine-3-carboxylate (66.7 mmol), 11.5 mL of 4-methyl-5-trifluoromethylaniline (80 mmol, 1.2 equiv.) and 141 mL of dry toluene under an atmosphere of nitrogen. Nitrogen was bubbled through the resultant solution for 10 minutes and then the solution was warmed to 30° C. The oil bath was removed and 100 mL of a 2 M solution of $AlMe_3$ in toluene (Aldrich, 200 mmol, 3 equiv.) was cannulated into the reaction mixture at a rate maintaining the reaction temperature between 35-40° C., a process that took approximately 45 minutes. The temperature of the reaction mixture was then increased to 55° C. over a period of 1 hour and the reaction mixture was stirred at 55° C. for 8 hours, whereupon all of the starting ester was consumed (monitored by LC-MS). The reaction was subsequently cooled overnight to ambient temperature and the solution was then cannulated into a mechanically stirred 1 L flask containing a solution of 67.8 g of sodium potassium tartrate tetrahydrate (240 mmol, 3.6 equiv.) in 237 mL of water, pre-cooled to 10° C. in an ice bath. The addition process took approximately 30 minutes, during which the reaction mixture self-heated to 57° C. The empty reaction flask was subsequently rinsed with 20 mL of dry toluene and the solution was combined with the quench mixture. The mixture was then cooled to r.t. with stirring, 91 mL of ethyl acetate was added, and the mixture was stirred an additional 15 minutes. The mixture was subsequently filtered through a pad of Celite and the filtrate was allowed to separate into two layers. The organic layer was then separated and washed with a solution of 5.7 g of sodium potassium tartrate tetrahydrate (20 mmol) in 120 mL of water and then with two 120 mL portions of water. The wet organic solution was concentrated in vacuo to a weight of ~150 g and a solvent exchange with ethanol was performed maintaining a total volume of 0.2-0.3 L, until <1 mol. % toluene with respect to ethanol was observed by $^1H$ NMR. The solution was then evaporated at elevated temperature to a weight of 223 g and heated to reflux. Mechanical stirring was initiated and 41 mL of water was added. The resulting solution was seeded with (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide crystals at 60° C. and then slowly cooled to r.t. over 2 hours. The slurry was subsequently stirred for 18 hours and the solids were filtered off. The solids were then washed with two 30 mL portions of 7:3 ethanol/water and dried in a vacuum oven for 24 hours at 50° C. to afford 31.0 g of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide as off-white crystals (80% yield). Analytical data: HPLC purity: 99.59%; >99.8% d.e. and e.e. by HPLC; ICP-OES Pd: <1 ppm; Al: 6 ppm; residual toluene by headspace GC-MS: 15 ppm; microash <0.1%; K-F 0.1%. $^1H$ NMR (400 MHz, TFA-d) δ 7.91 (d, J=8.6 Hz, 1H), 7.84 (d, J=8.6 Hz, 1H), 7.58-6.82 (m, 8H), 6.75 (t, J=8.6 Hz, 1H), 4.10-4.00 (m, 1H), 3.60-3.47 (m, 1H), 3.45-3.41 (m, 1H), 3.33-3.25 (m, 1H), 2.44-2.22 (m, 7H), 2.04-1.92 (m, 4H), 1.82-1.69 (m, 7H), MS: (ES) m/z 582 (M+H⁺).

Example 2

Figure 2:
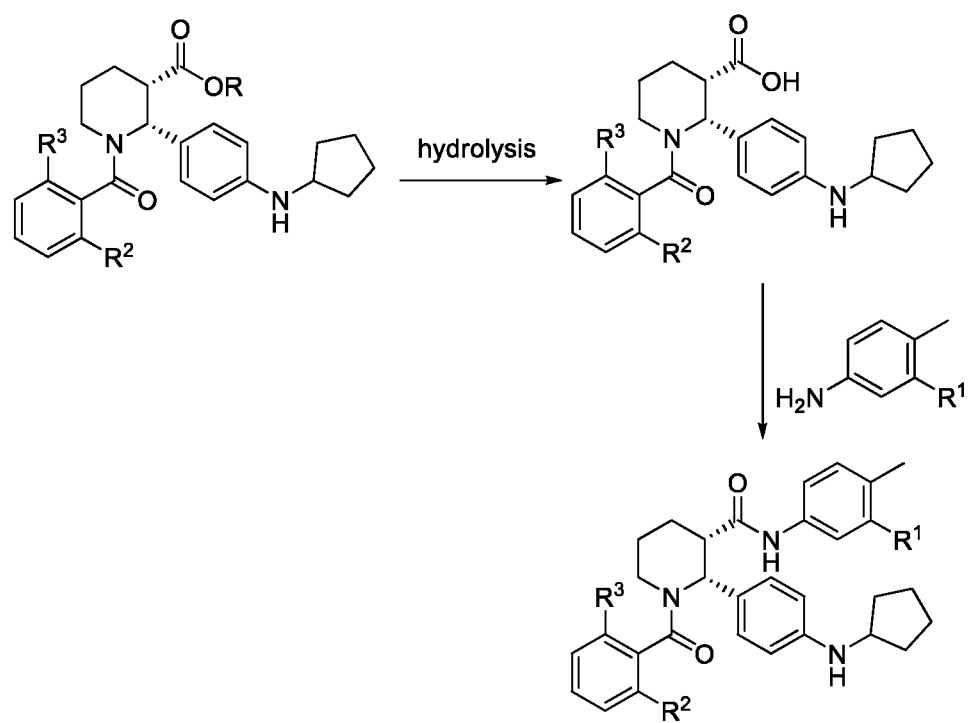
FIG. 2 provides a scheme in which the C3 amide formation (final step of Scheme 1) is carried out via conversion of a C3 ester to a C3 carboxylic acid—which upon treatment with a suitable aniline can provide compounds such as IA, IB and IC.

This example illustrates the preparation of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide by the general method provided in FIG. 2 (Scheme 2) using the reagents shown in Route 2:

Route 2:

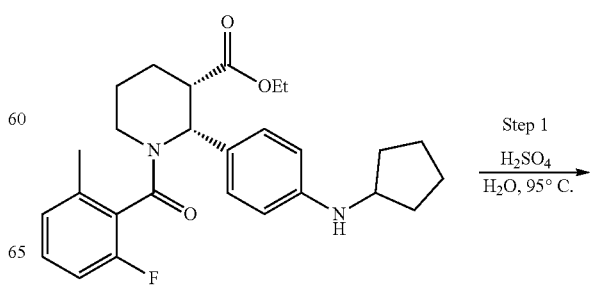

Step 1
$H_2SO_4$
$H_2O$, 95° C.

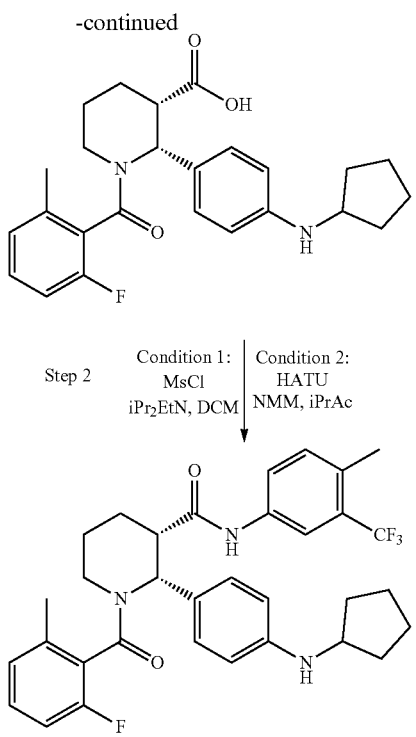

Step 1:

Solid ethyl (2R,3S)-2-[4-(cyclopentylamino)phenyl]-1-(2-fluoro-6-methyl-benzoyl)piperidine-3-carboxylate (316 g, 0.698 mol) was added portionwise to a 12 L flask containing mechanically stirred 2.80 L of 0.44 M H₂SO₄ in water heated to 70° C. 0.36 L of additional 0.44 M H₂SO₄ was used to wash the solids down from the funnel. The suspension was brought to 95° C. and stirred at this temperature for 21 hours, whereupon full dissolution has occurred and no more than 4% of starting material was remaining. The reaction was cooled down to ambient temperature. To the mixture were added 2.80 L of 1 M NaOH in water over a period of 30 minutes maintaining the temperature around 20° C., followed by 1.58 L of MTBE and again 1.40 L of 1M NaOH. The mixture was vigorously stirred for 1 hour until all the solids were dissolved (final pH was 13.1). The layers were separated and the organic layer was discarded. The aqueous layer was again extracted with 1.58 L of MTBE. The aqueous layer was concentrated in vacuo to remove excess MTBE. The solution was transferred back to the mechanically stirred flask and the solution was acidified with 1 M H₂SO₄ over 25 minutes until a pH of 4.8 was reached (approximately 0.71 L of 1M H₂SO₄) and the resultant mixture was stirred at ambient temperature for 1 h. The slurry was filtered and the solids were washed with two 2.0 L portions of water followed by 1.0 L of heptane. The solid was dried in a vacuum oven at 45° C. to give 279 g of (2R,3S)-2-[4-(cyclopentylamino)phenyl]-1-(2-fluoro-6-methyl-benzoyl)piperidine-3-carboxylic acid as a white solid (94% yield).

Step 2, Condition 1:

To a 12 L flask containing (2R,3S)-2-[4-(cyclopentylamino)phenyl]-1-(2-fluoro-6-methyl-benzoyl)piperidine-3-carboxylic acid (277 g, 0.652 mol) in 1.66 L of dichloromethane was added 4-methyl-3-(trifluoromethyl)aniline (112 mL, 137 g, 0.782 mol, 1.2 equiv.) followed by N,N-diisopropylethylamine (204 mL, 152 g, 1.17 mol, 1.8 equiv.). The solution was cooled to 0° C. and methanesulfonyl chloride (65.6 mL, 97.1 g, 0.848 mol, 1.3 equiv.) was added dropwise. After stirring for 18 hours at ambient temperature N,N-diisopropylethylamine (114 mL, 84.2 g, 0.652 mol, 1.0 equiv.) was added. The reaction mixture was stirred at ambient temperature for 15 minutes and 2.22 L of isopropyl acetate and 0.55 L of DCM were added to the flask. The solution was washed with 2.22 L of water and then again with 1.11 L of water. The organic layer was washed twice with 2.22 L portions of 0.1M sodium hydroxide in water. 139 g of anhydrous sodium sulfate was added to the organic layer and stirred for 15 minutes. To the suspension 544 g of silica gel (230-400 mesh) was added and the mixture was stirred for 30 minutes. The suspension was filtered using a tall fritted funnel and the silica gel bed was washed on the funnel with 2.50 L of isopropyl acetate/DCM (1:1). The combined solution was concentrated in vacuo at 40° C. to an approximate weight of 760 g. The flask was equipped with a mechanical stirrer at which point spontaneous crystallization commenced. After 15 minutes of stirring 1.14 L of heptane was added to the suspension over a period of 20 minutes. 16 hours of stirring at ambient temperature yielded colorless crystals, which were filtered off and sequentially washed on the funnel with two portions of heptane (0.76 L and 0.38 L). The solids were dried in a vacuum oven for 16 h at 45° C. to afford 289 g of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide as colorless crystals (76% yield, e.e. 98.6%, 1.4 wt. % of isopropyl acetate (by ¹H NMR); 98.1% purity by HPLC at 220 nm). ¹H NMR (400 MHz, TFA-d) δ 7.91 (d, J=8.6 Hz, 1H), 7.84 (d, J=8.6 Hz, 1H), 7.58-6.82 (m, 8H), 6.75 (t, J=8.6 Hz, 1H), 4.10-4.00 (m, 1H), 3.60-3.47 (m, 1H), 3.45-3.41 (m, 1H), 3.33-3.25 (m, 1H), 2.44-2.22 (m, 7H), 2.04-1.92 (m, 4H), 1.82-1.69 (m, 7H), MS: (ES) m/z 582 (M+H⁺).

Step 2, Condition 2:

To a 250 mL flask containing (2R,3S)-2-[4-(cyclopentylamino)phenyl]-1-(2-fluoro-6-methyl-benzoyl)piperidine-3-carboxylic acid (8.01 g, 18.8 mmol) in 40 mL of isopropyl acetate was added 4-methyl-3-(trifluoromethyl)aniline (2.97 mL, 3.62 g, 20.7 mmol, 1.1 equiv.) followed by N-methylmorpholine (3.10 mL, 2.85 g, 28.2 mmol, 1.5 equiv.) and HATU (9.29 g, 24.4 mol, 1.3 equiv.). After stirring for 44 hours at ambient temperature the reaction mixture was diluted with 100 mL of isopropyl acetate and 60 mL of water and stirred for 15 minutes. The undissolved solids were filtered off and the aqueous layer was discarded. The organic phase was washed twice with 60 mL of water and then concentrated in vacuo to a weight of 58 g. The solvent was then exchanged with ethanol by co-distillation and the solution was concentrated in vacuo to a weight of 74 g (0.6 wt. % of isopropyl acetate remaining). The mixture was heated to reflux and 14 mL of water was added. The resulting solution was seeded with (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide crystals at 60° C. and then slowly cooled to r.t. over 2 hours. The slurry was subsequently stirred for 18 hours and the solids were filtered off. The solids were then washed with two 8 mL portions of 7:3 ethanol/water and dried in a vacuum oven for 24 hours at 50° C. to afford 7.91 g of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide as colorless crystals (72% yield). Analytical data: HPLC purity: 99.26%; >99.8% d.e. and e.e. by HPLC. ¹H NMR (400 MHz, TFA-d) δ 7.91 (d, J=8.6 Hz, 1H), 7.84 (d, J=8.6 Hz, 1H), 7.58-6.82 (m, 8H), 6.75 (t, J=8.6 Hz, 1H), 4.10-

4.00 (m, 1H), 3.60-3.47 (m, 1H), 3.45-3.41 (m, 1H), 3.33-3.25 (m, 1H), 2.44-2.22 (m, 7H), 2.04-1.92 (m, 4H), 1.82-1.69 (m, 7H), MS: (ES) m/z 582 (M+H$^+$).

Example 3

Figure 3:
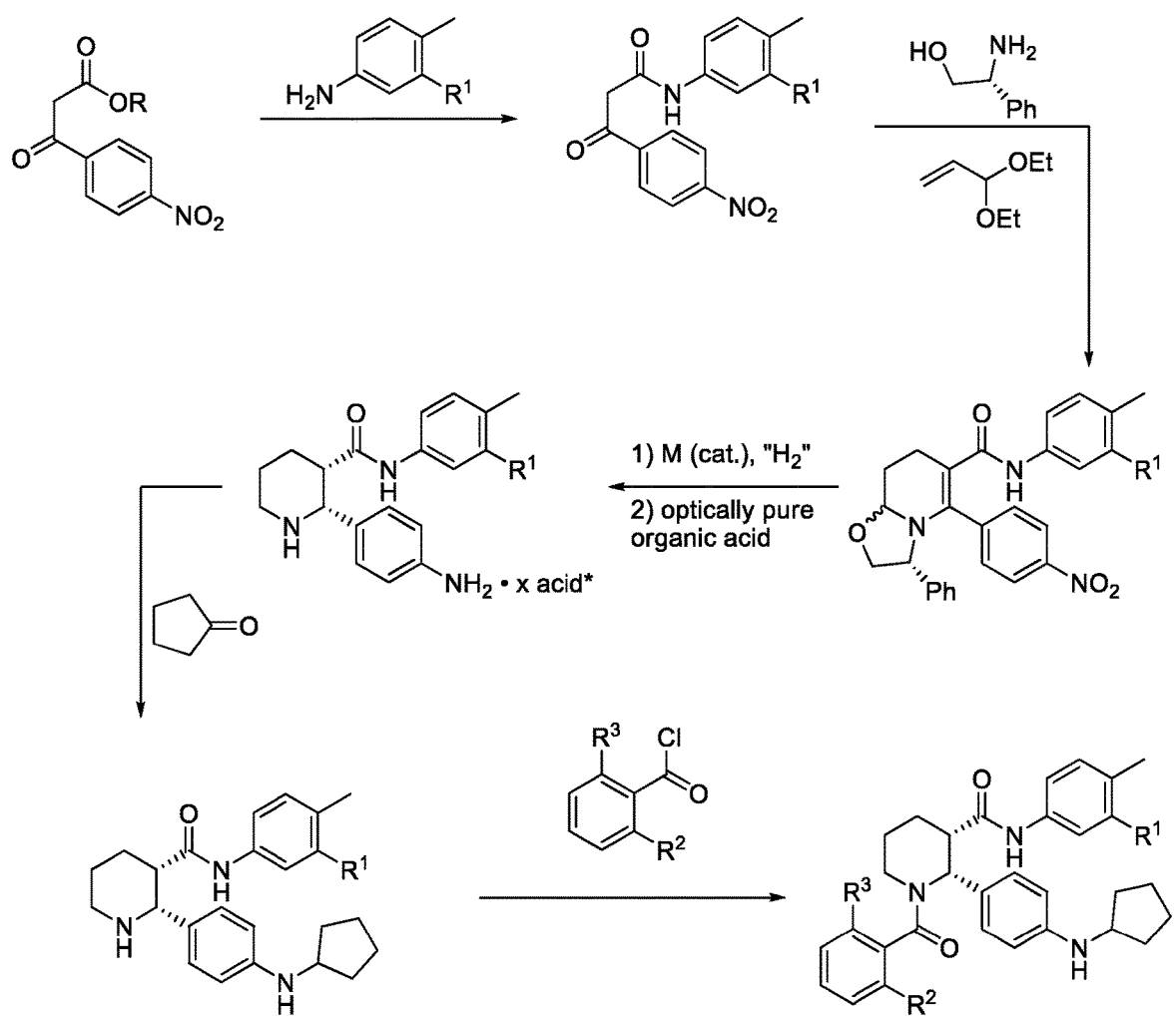
FIG. 3 provides a scheme in which the C3 amide is constructed at an earlier stage of synthesis, followed by steps in which hydrogenation is used to set the (2R,3S) stereochemistry, followed by a reductive amination of cyclopentanone, and concluding with benzoylation of the piperidine nitrogen to provide compounds such as IA, IB and IC.
Figure 4:
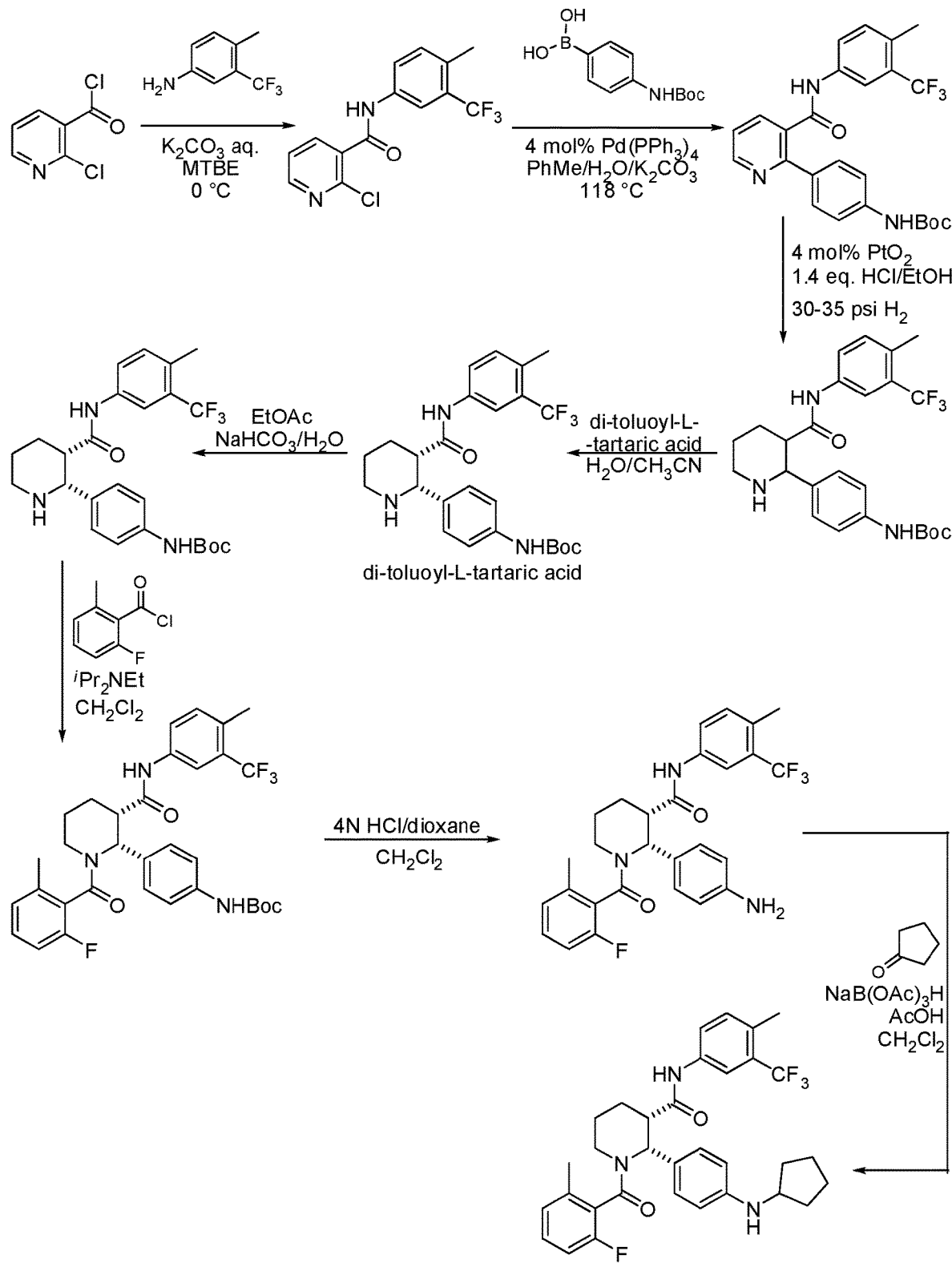
FIG. 4 provides a scheme for the preparation of IA as described in U.S. Pat. No. 8,445,515 B2, utilizing a classical resolution step to prepare compound 7 having (2R,3S) stereochemistry.

This example illustrates the preparation of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide by the general method provided in FIG. 3 (Scheme 3), using the reagents shown in Route 3:

Route 3:

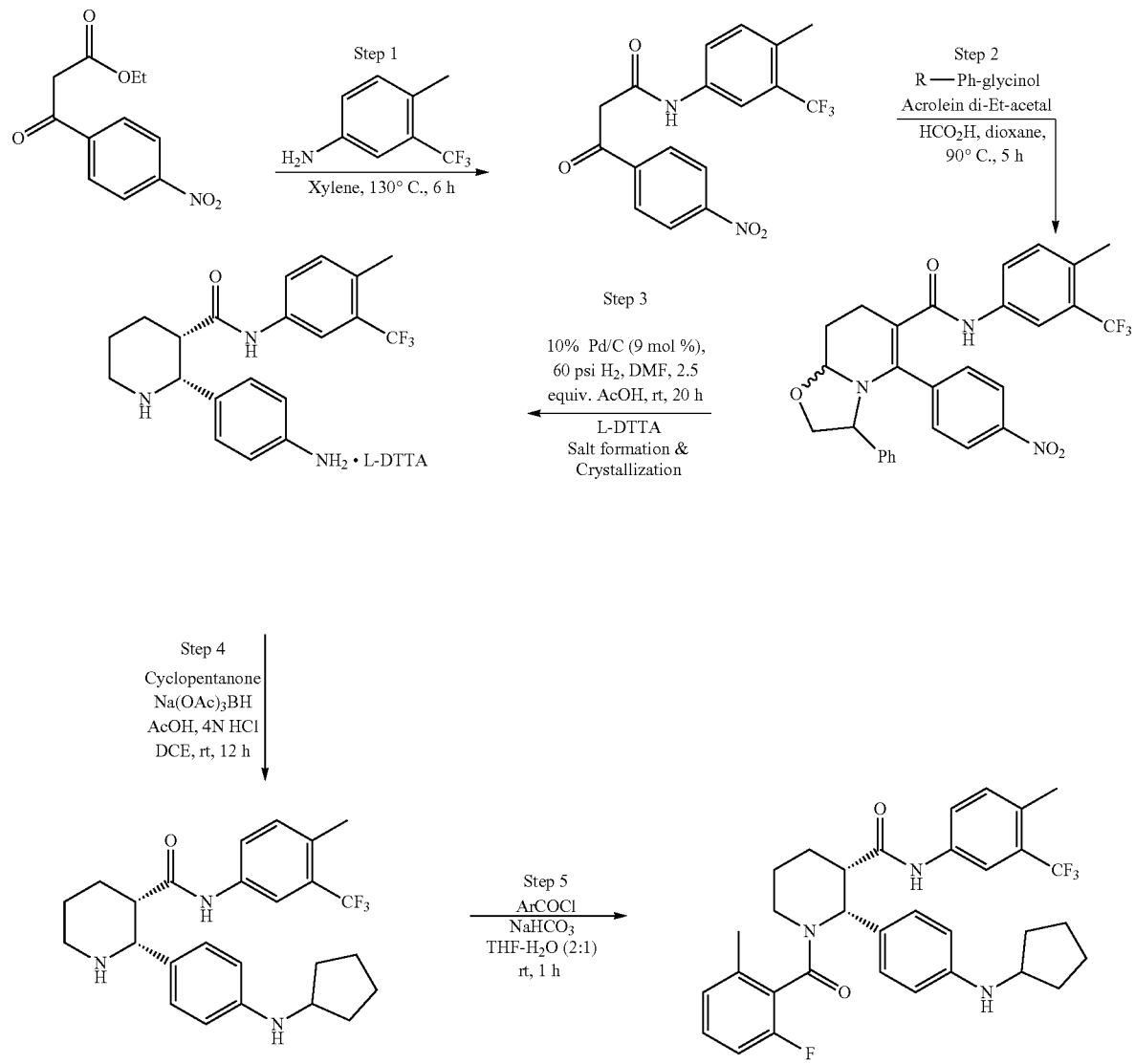

Step 1:

To a 500 mL, 3-necked, round bottom flask equipped with a thermometer was added ethyl 3-(4-nitrophenyl)-3-oxo-propanoate (50 g, 211 mmol), o-xylene (100 mL) followed by 4-methyl-3-(trifluoromethyl)aniline (33.25 mL, 232 mmol) and the resulting reaction mixture was stirred at 130° C. for 6 h (ethanol generated during the reaction was removed using a distillation condenser as it was formed).

The reaction mixture was cooled to room temperature and aged overnight. Obtained crystals were collected by filtration, washed with diethyl ether (500 mL), dried under high vacuum to obtain N-[4-methyl-3-(trifluoromethyl)phenyl]-3-(4-nitrophenyl)-3-oxo-propanamide (74.4 g) in 96% yield as bright yellow crystalline solid. $^1$H NMR showed ~2:1 mixture of keto-enol tautomers. $^1$H NMR (400 MHz, DMSO-d$_6$) δ 10.61 (bs, 1H), 10.48 (s, 1H), 8.37-8.31 (m, 2H), 8.21 (d, J=9 Hz, 1H), 8.0-7.95 (m, 2H), 7.65 (dd, J=21.2, 8.2 Hz, 1H), 7.37 (dd, J=13.3, 8.2 Hz, 1H), 6.06 (s, 1H), 4.25 (s, 2H), 2.37, 2.36 (2s, 3H); MS: (ES) m/z 367 (M+H$^+$).

Step 2:

A mixture of (R)-(−)-2-phenylglycinol (3.02 g, 22 mmol), N-[4-methyl-3-(trifluoromethyl)phenyl]-3-(4-nitrophenyl)-3-oxo-propanamide (7.32 g, 20 mmol), acrolein diethyl acetal (4 mL, 28.6 mmol) and formic acid (0.8 mL, 20 mmol) in p-dioxane (10 mL) was stirred at 90° C. for 4 h. The reaction mixture was cooled to room temperature, diluted with dichloromethane (20 mL), adsorbed on silica gel and purified by column chromatography (product was eluted with 30% ethyl acetate in hexanes) to obtain (3R)—N-[4-methyl-3-(trifluoromethyl)phenyl]-5-(4-nitrophenyl)-3-phenyl-3,7,8,8a-tetrahydro-2H-oxazolo[3,2-a]pyridine-6-carboxamide (8.4 g) in 80% yield as yellow foam with diastereomeric ratio of ~3:2. $^1$H NMR (400 MHz, CDCl$_3$) δ 7.96-786 (bs, 1H), 7.20-7.15 (m, 3H), 7.15-7.0 (m, 6H), 6.9 (dd, J=7.81, 1.57 Hz, 1H), 6.7 (d, J=8.6 Hz, 1H), 6.44 (d, J=29.7 Hz, 1H), 5.26 (dd, J=8.6, 3.5 Hz, 0.6H), 5.06 (dd, J=9.77, 2.73 Hz, 0.4H), 4.48 (d, J=6.25 Hz, 0.5H), 4.36-4.28 (m, 1H), 4.22-4.17 (m, 0.5H), 4.02 (dd, J=8.99, 1.56 Hz, 0.5H), 3.8 (dd, J=8.6, 5.08 Hz, 0.5H), 3.2-2.8 (m, 1H), 2.7-2.4 (m, 2H), 2.14 (s, 3H), 1.95-1.85 (m, 1H); MS: (ES) m/z 524 (M+H$^+$).

Step 3:

(3R)—N-[4-methyl-3-(trifluoromethyl)phenyl]-5-(4-nitrophenyl)-3-phenyl-3,7,8,8a-tetrahydro-2H-oxazolo[3,2-a]pyridine-6-carboxamide (2.1 g, 4 mmol), DMF (12 mL), palladium catalyst (10% Pd/C, Degussa type E101 NE/W, 50% wet, 800 mg, 45 wt % of powder, 0.36 mmol) and acetic acid (0.6 mL, 10 mmol) were placed in a Parr bottle and agitated under hydrogen gas (60 psi) for 20 hours at ambient temperature. The reaction mixture was passed through a frit to remove palladium catalyst, washed with methanol (2×20 mL) and evaporated to dryness on rotavapor in vacuo to obtain the crude product. To this crude product was added wthyl acetate (30 mL), dichloromethane (60 mL), (−)-O,O'-di-p-toluoyl-L-tartaric acid (L-DTTA, 1.55 g, 4 mmol) and the resulting mixture was aged at room temperature overnight. Obtained crystals were collected by filtration, washed with cold ethyl acetate (2×10 mL) and dried under high vacuum to obtain (2R,3S)-2-(4-aminophenyl)-N-[4-methyl-3-(trifluoromethyl)phenyl]piperidine-3-carboxamide as 1:1 L-DTTA salt (1.32 g) in 43% yield with enantiomeric ratio of 98:2 (chiral column: Regis Cell, HPLC system: Agilent 1200 Series Model G1312A, solvent: 0.1% diethylamine in MeOH, isocratic, flow rate: 1 mL/min, ambient temperature, retention time for major isomer: 6.86 min). $^1$H NMR (400 MHz, CD$_3$OD) δ 8.01 (d, J=6.6 Hz, 4H), 7.88 (d, J=2.35 Hz, 1H), 7.5 (dd, J=8.4, 2.34 Hz, 1H), 7.28 (d, J=7.8 Hz, 2H), 7.26 (d, J=8.99 Hz, 2H), 7.14 (d, J=8.6 Hz, 2H), 6.68 (d, J=8.6 Hz, 2H), 5.87 (s, 2H), 4.35 (d, J=3.12 Hz, 1H), 3.52-3.58 (m, 1H), 3.06-3.23 (m, 2H), 2.40 (s, 9H), 2.18-2.12 (m, 2H), 1.84 (d, J=14.46 Hz, 1H); MS: (ES) m/z 378 (M+H$^+$).

Step 4:

To (2R,3S)-2-(4-aminophenyl)-N-[4-methyl-3-(trifluoromethyl)phenyl]piperidine-3-carboxamide (−)-O,O'-di-p-toluoyl-L-tartaric acid salt (1:1) (15.17 g, 19.85 mmol) in dichloromethane (100 mL) was added cyclopentanone (1.93 mL, 21.84 mmol), 4 N HCl in p-dioxane (6.31 mL, 25.24 mmol) and acetic acid (3.57 mL, 59.55 mmol) followed by sodium triacetoxyborohydride (6.31 g, 29.78 mmol) at room temperature and the resulting reaction mixture was stirred at room temperature overnight. Saturated sodium bicarbonate solution (100 mL) was added slowly and the organic layer was separated. Aqueous layer was further extracted with dichloromethane (2×100 mL) and combined organic layers were dried over anhydrous sodium sulfate and concentrated in vacuo to obtain crude (2R,3S)-2-[4-(cyclopentylamino)phenyl]-N-[4-methyl-3-(trifluoromethyl)phenyl]piperidine-3-carboxamide (9.5 g) which was used as such in the next step without further purification. $^1$H NMR (400 MHz, CD$_3$OD) δ 7.71 (d, J=1.96 Hz, 1H), 7.43 (dd, J=8.2, 1.95 Hz, 1H), 7.22 (d, J=8.6 Hz, 1H), 7.08 (d, J=8.6 Hz, 2H), 6.58 (d, J=8.6 Hz, 2H), 3.88 (d, J=3.52 Hz, 1H), 3.69 (q, J=12.1, 6.3 Hz, 1H), 3.33-3.35 (m, 1H), 2.88-2.78 (m, 2H), 2.39 (s, 3H), 2.16-1.85 (m, 5H), 1.75-1.5 (m, 5H), 1.45-1.35 (m, 2H); MS: (ES) m/z 446 (M+H$^+$).

Step 5:

To a flask containing a solution of sodium bicarbonate (1.9 g, 22.62 mmol) in 45 mL of water was added a solution of crude (2R,3S)-2-[4-(cyclopentylamino)phenyl]-N-[4-methyl-3-(trifluoromethyl)phenyl]piperidine-3-carboxamide (5.0 g, 11.23 mmol) in 90 mL of tetrahydrofuran over a period of 10 minutes. The resulting mixture was stirred at ambient temperature for 1 hour. 2-Fluoro-6-methylbenzoyl chloride (1.73 g, 8.98 mmol) in 5 mL of tetrahydrofuran was added dropwise over 10 minutes. Upon completion of the reaction, the undissolved solid was filtered off and the filtrate was concentrated in vacuo. Heptane (50 mL) was added to the remaining aqueous layer and the mixture was vigorously stirred for 16 h at room temperature. The contents were filtered and the solid was washed with water (2×30 mL) followed by heptane (30 mL). The solid was dried under high vacuum to obtain crude product (3.68 g) which was dissolved in ethanol (22 mL) with gentle heating and then water (4 mL) was added. Obtained brown colored clear solution was cooled to room temperature and stirred overnight. Crystals were collected by filtration, washed with cold ethanol (5 mL), dried under high vacuum to get (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (1.66 g) in 28% yield for two steps with enantiomeric ratio of 98:2 (chiral column: Pirkle Covalent, (S,S) Whelk-O1, 5/100, 25 cm×4.6 mm Kromasil, S/N 50404, HPLC system: Agilent 1200 Series Model G1312A, solvent: 15% hexanes in iso-propanol, isocratic, flow rate: 1 mL/min, column temperature: 75° C., retention time of major isomer: 9.9 min). $^1$H NMR (400 MHz, TFA-d) δ 7.91 (d, J=8.6 Hz, 1H), 7.84 (d, J=8.6 Hz, 1H), 7.58-6.82 (m, 8H), 6.75 (t, J=8.6 Hz, 1H), 4.10-4.00 (m, 1H), 3.60-3.47 (m, 1H), 3.45-3.41 (m, 1H), 3.33-3.25 (m, 1H), 2.44-2.22 (m, 7H), 2.04-1.92 (m, 4H), 1.82-0.169 (m, 7H); MS: (ES) m/z 582 (M+H$^+$).

Example 4

This example illustrates the synthesis of (2R,3S)-2-[4-(cyclopentylamino)phenyl]-1-(2-fluoro-6-methyl-benzoyl)-N-[4-methyl-3-chlorophenyl]piperidine-3-carboxamide:

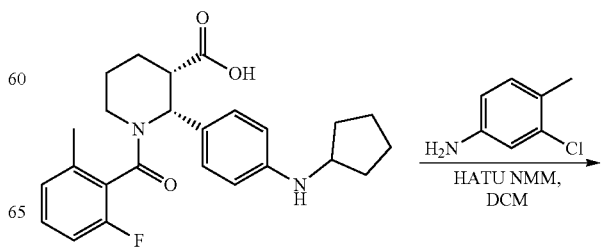

-continued

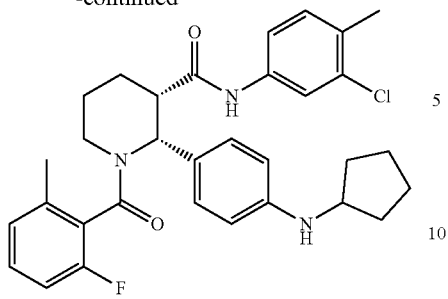

To a 100 mL flask containing (2R,3S)-2-[4-(cyclopentylamino)phenyl]-1-(2-fluoro-6-methyl-benzoyl)piperidine-3-carboxylic acid (2.71 g, 6.38 mmol) in 20 mL of dichloromethane was added 3-chloro-4-methylaniline (0.85 mL, 7.01 mmol, 1.1 equiv.) followed by N-methylmorpholine (1.05 mL, 968 mg, 9.57 mmol, 1.5 equiv.) and HATU (2.91 g, 7.66 mol, 1.2 equiv.). After stirring for 24 hours at ambient temperature the reaction mixture was concentrated in vacuo, diluted with 50 mL of isopropyl acetate and 20 mL of water and stirred for 15 minutes. The undissolved solids were filtered off and the aqueous layer was discarded. The organic phase was washed twice with 20 mL of water and then concentrated in vacuo to dryness. The solids were evaporated twice with 30 mL of ethanol. The resulting residue was then dissolved in 22 mL of refluxing ethanol and 4 mL of water was added. The resulting solution was then refluxed for 15 minutes (until initial seed bed was formed) and then slowly cooled to r.t. The slurry was subsequently stirred for 3 hours and the solids were filtered off. The solids were then washed with 10 mL of 7:3 ethanol/water and dried in a vacuum oven for 24 hours at 50° C. to afford 2.95 g of (2R,3S)-2-[4-(cyclopentylamino)phenyl]-1-(2-fluoro-6-methyl-benzoyl)-N-[4-methyl-3-chlorophenyl]piperidine-3-carboxamide as colorless crystals (84% yield).

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A process for the preparation of compounds of formula (I), or a pharmaceutically acceptable salt thereof:
   (a') reacting an ester of 3-(4-nitrophenyl)-3-oxo-propanoate (i-1, or ii-1, wherein R is selected from the group consisting of $C_{1-8}$ alkyl, aryl and aryl-$C_{1-4}$ alkyl) with 3-chloro-4-methylaniline or 3-trifluoromethyl-4-methylaniline under conditions sufficient to provide a compound of formula (ii-2);

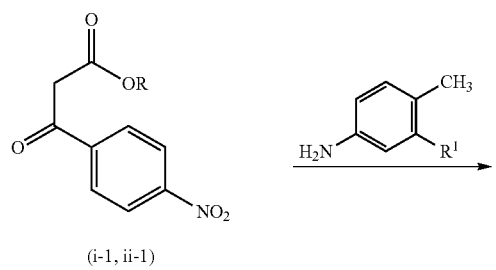

(i-1, ii-1)

(b') reacting (ii-2), (R)-(−)-2-phenylglycinol, and acrolein diethyl acetal or an equivalent thereof, to produce compound (ii-3);

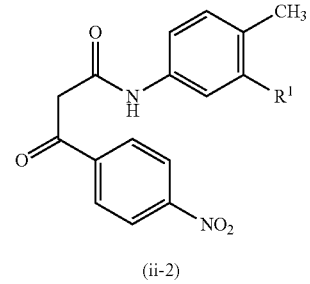

(ii-2)

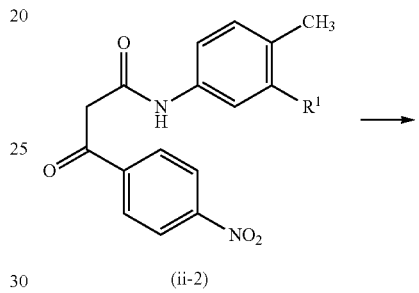

(ii-2)

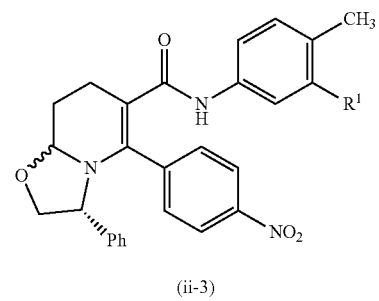

(ii-3)

(c') reducing (ii-3) under conditions sufficient to produce an intermediate diamine (ii-4) that is substantially free of enantiomeric or diastereomeric impurities;

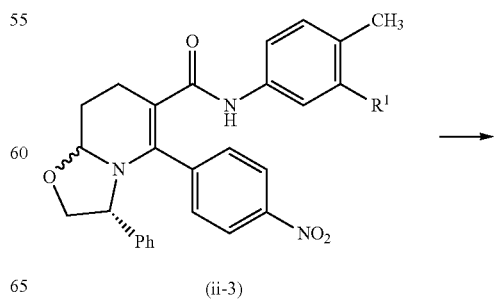

(ii-3)

-continued
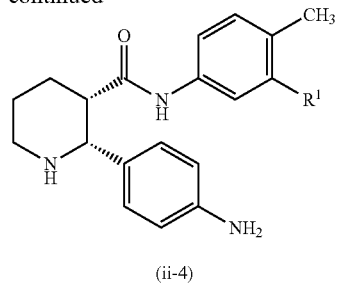
(ii-4)
(d') converting (ii-4) to (ii-5) with cyclopentanone and a reducing agent; and
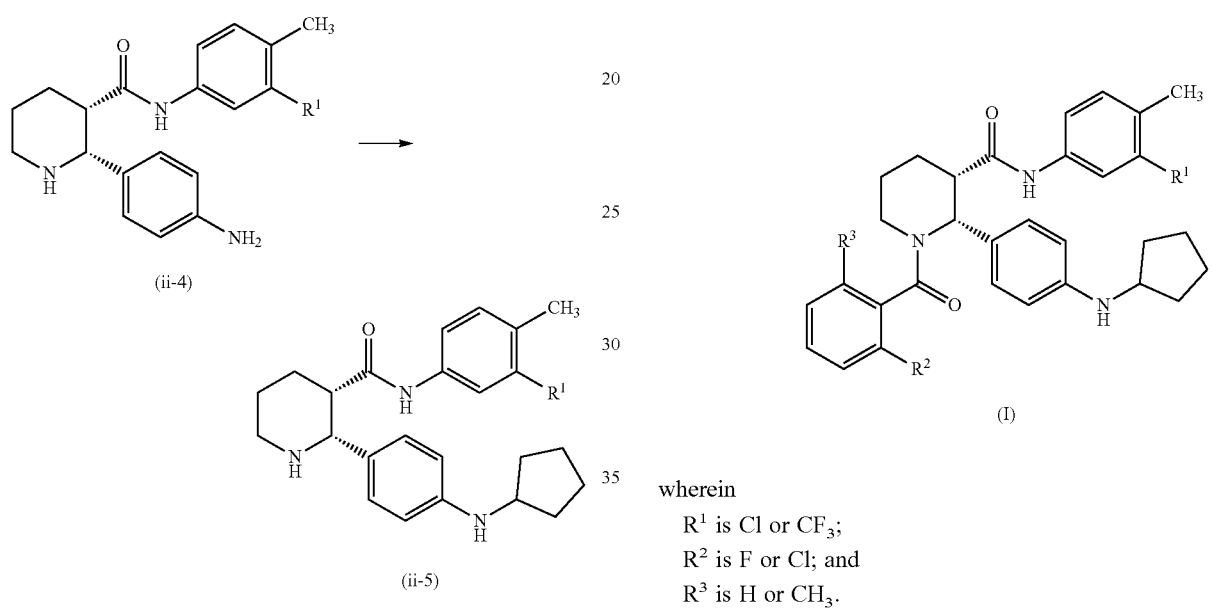
(e') combining (ii-5) with either 2-fluoro-6-methylbenzoyl chloride or 2-chlorobenzoyl chloride to provide (I);
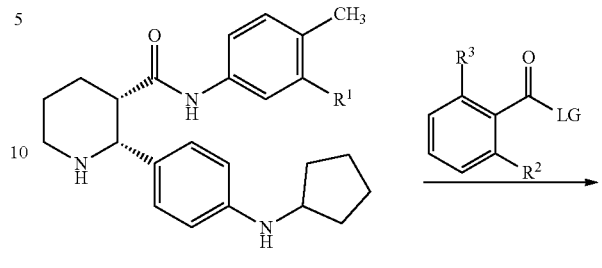
wherein
R$^1$ is Cl or CF$_3$;
R$^2$ is F or Cl; and
R$^3$ is H or CH$_3$.
* * * * *